US005935823A

United States Patent [19]
Fowlkes et al.

[11] Patent Number: 5,935,823
[45] Date of Patent: Aug. 10, 1999

[54] TOTALLY SYNTHETIC AFFINITY REAGENTS

[75] Inventors: Dana M. Fowlkes; Brian K. Kay, both of Chapel Hill, N.C.

[73] Assignee: The University of North Carolina at Chapel Hill, Chapel Hill, N.C.

[21] Appl. No.: 08/420,945

[22] Filed: Apr. 11, 1995

Related U.S. Application Data

[63] Continuation of application No. 08/022,236, Feb. 25, 1993, abandoned, which is a continuation of application No. 07/854,133, Mar. 19, 1992, abandoned, which is a continuation of application No. 07/480,420, Feb. 15, 1990, abandoned.

[51] Int. Cl.⁶ ..................................... C12P 21/04
[52] U.S. Cl. ..................... 435/69.7; 435/172.3; 530/300; 530/350; 530/387; 530/412; 530/333
[58] Field of Search ............................... 435/69.7, 172.3; 530/350, 300, 387, 412, 333

[56] References Cited

U.S. PATENT DOCUMENTS

| | | |
|---|---|---|
| 4,732,864 | 3/1988 | Tolman . |
| 5,096,815 | 3/1992 | Ladner et al. . |
| 5,198,346 | 3/1993 | Ladner et al. . |
| 5,223,409 | 6/1993 | Ladner et al. ...................... 435/69.1 |

FOREIGN PATENT DOCUMENTS

| | | |
|---|---|---|
| 035384 | 9/1981 | European Pat. Off. . |
| 2 183 661 | of 0000 | United Kingdom . |
| 2183661 | 6/1987 | United Kingdom . |
| WO 86/05803 | 10/1986 | WIPO . |
| WO 88/06630 | 9/1988 | WIPO . |
| WO 8806630 PCT/US89/ | 9/1988 | WIPO . |
| 03267 | 2/1990 | WIPO . |

OTHER PUBLICATIONS

Parmley et al. 1988 GENE 73:305–318.
Pamley et al. 1988 Adv. Exp. Med. Biol. 251:215–218.
Dunn et al., 1988, Protein Eng. 2:283–291.
Horwitz and Loeb, 1986, Proc. Natl. Acad. Sci. USA 83:7405–7409.
Huse et al., 1989, Science 246:1275–1281.
Hutchison et al., 1986, Proc. Natl. Acad. Sci. USA 83:710–714.
Huynh et al., 1985, Glover ed., DNA Cloning: A Practical Approach, vol. 1, IRL Press, pp. 49–78.
Kemp and Cowman, 1981, Proc. Natl. Acad. Sci. USA 78:4520–4524.
Mandecki, 1990, Protein Eng. 3:221–226.
Matteucci and Heyneker, 1983, Nucleic Acids Res. 11:3113–3121.
McNeil et al., 1985, Mol. Cell. Biol. 5:3545–3551.
Min et al., 1988, Nucleic Acids Res. 16:5075–5088.
Oliphant et al., 1986, Gene 44:177–183.

Sambrook, Fritsch, and Maniatis, "Analysis and Cloning of Eukaryotic Genomic DNA," Chapter 9 in Cloning, A Laboratory Manual, 2d ed., Cold Spring Harbor Laboratory Press, 1989, pp. 9.2–9.62.
Sambrook, Fritsch, and Maniatis, "Construction and Analysis of cDNA Libraries," Chapter 8 in Cloning, A Laboratory Manual, 2d ed., Cold Spring Harbor Laboratory Press, 1989, pp. 8.2–8.86.
Sambrook, Fritsch, and Maniatis, "Screening Expression Libraries with Antibodies and Oligonucleotides," Chapter 12 in Cloning, A Laboratory Manual, 2d ed., Cold Spring Harbor Laboratory Press, 1989, pp. 12.2–12.44.
Sambrook, Fritsch, and Maniatis, Cloning, A Laboratory Manual, 2d ed., Cold Spring Harbor Laboratory Press, 1989, pp. 2.55, 2.57–2.59.
Schneider and Stormo, 1989, Nucleic Acids Res. 17:659–674.
Smith, 1985, Science 228:1315–1317.
Snouwaert et al., 1987, Nucl. Acids Res. 15:8293–8303.
Young and Davis, 1983, Proc. Natl. Acad. Sci. USA 80:1194–1198.
U.S. application No. 07/240,160, Ladner et al., filed Sep. 2, 1988.
Huse et al., Science 246: 1275–1281 (1989).
Baldwin and Schultz, Science 245: 1104–1107 (1989).
Query et al., Cell 57: 89–101 (1989).
Chaudhary et al., Proc. Natl. Acad. Sci. 87: 1066–1070 (1990).
Pabo and Sauer, Ann. Rev. Biochem. 53: 293 (1984).
Landschultz et al., Science 240: 1759 (1988).
Berg, Science 232: 485 (1986).
Miller et al., EMBO J. 4: 1609 (1985).
Honzatkio et al., J. Mol. Biol. 160: 219 (1982).
Cherny et al., Proc. Natl. Acad. Sci. 84: 8370 (1987).
Metallothioneins, pp. 46–92 eds. Kagi and Nordberg, Birkhauser Verlag Basel (1979).
Grill et al., Science 230: 674 (1985).
Jurnak, Science 230: 32 (1985).
la Cour et al., EMBO J. 4: 2385 (1985).
McCormick et al., Science 230: 78 (1985).
Rao and Rossmann, J. Mol. Biol. 76: 241 (1973).
Kretsinger and Nickolds, J. Biol. Chem. 248: 3313 (1973).
Sharma et al., J. Biol. Chem. 264: 12794 (1989).
Ruoslahti and Pierschbacher, Cell 44: 517 (1986).
Pytola et al., Cell 40: 191 (1985).
Pytola et al., Science 231: 1559 (1986).
Ruoslahti and Pierschbacher, Science 238: 491 (1987).
Graf et al., Cell 48: 989 (1987).
Cabilly et al., Proc. Natl. Acad. Sci. 81: 3273 (1984).
Guarente et al., Cell 20: 543 (1980).
Morrison et al., Proc. Natl. Acad. Sci. 81: 6851 (1984).
Jones et al., Nature 321: 522 (1986).
Riechmann et al., J. Mol. Biol. 203: 825 (1988).
Matteucci and Heyneker, Nucl. Acids Res. 11: 3113 (1983).
Wells et al., Gene 34: 315 (1985).
McNeil and Smithy, Mol. Cell. Biol. 5: 3545 (1985).
Oliphant et al., Gene 44: 177 (1986).
Hutchinson et al., Proc. Natl. Acad. Sci. 83: 710 (1986).
Derbyshire et al., Gene 46: 145 (1986).
Snouwaert et al., Nucl. Acids Res. 15: 8293 (1987).
Morrison, 1985, Science 229: 1202–1207.
Williams et al., 1986, Gene 43: 319–324.
Neuberger et al., 1984, Nature 312: 604–608.
Reidhaar–Olson et al., 1988, Science 241: 53–57.
Nagai et al., 1984, Nature 309: 810–812.

Houghten et al., 1991, "General and use of synthetic peptide combinatorial libraries for basic research and drug discovery," Nature 354:84–86.

Lam et al., 1991, "A new type of synthetic peptide library for identifying ligand–binding activity," Nature 354:82–84.

Parmley and Smith, 1988, "Antibody–selectable filamentous fd phage vectors: affinity purification of target genes," Gene 73:305–318.

*Primary Examiner*—Stephen Walsh
*Assistant Examiner*—Kenneth A. Sorensen
*Attorney, Agent, or Firm*—Morgan & Finnegan LLP

[57] ABSTRACT

A novel process for producing novel and/or improved heterofunctional binding fusion proteins termed Totally Synthetic Affinity Reagents (TSARS) is disclosed. TSARs are concatenated heterofunctional polypeptides or proteins comprising at least two functional regions: a binding domain with affinity for a ligand and a second effector peptide portion that is chemically or biologically active. In one embodiment, the heterofunctional polypeptides or proteins further comprise a linker peptide portion between the binding domain and the second active peptide portion. The linker peptide can be either susceptible or not susceptible to cleavage by enzymatic or chemical means. Novel and/or improved heterofunctional binding reagents as well as methods for using the reagents for a variety of in vitro and in vivo applications are also disclosed.

17 Claims, 11 Drawing Sheets

```
            NcoI
    AATTCCATGGGTGTTCAGCTCCAGCAGCCGGGGTTCTGAACTCGTTCGCCCGGGTGCTTCT
      ------+---------+---------+---------+---------+---------+      60
         MetGlyValGlnLeuGlnLeuGlnProGlySerGluLeuValArgProGlyAlaSer
      ttaaggTACCCACAAGTCGAGGTCGTCGGCCCAAGACTTGAGCAAGCGGGCCCACGAAGA
  1

GTTAAACTCTCTTGCAAAGGCGTCTGGTTACACCTTCACTCTTACTGGATGCACTGGGTT
      ------+---------+---------+---------+---------+---------+      120
         ValLysLeuSerCysLysAlaSerGlyTyrThrPheThrSerTyrTyrTrpMetHisTrpVal
      CAATTTGAGAGAACGTTTCGCAGACCAATGTGGAAGTGGAGAATGACCTACGTGACCCAA
 61

XhoI
    AAACAACGTCCGGGTCAAGGTCTCGAGTGGATCGGTAACATCTATCCGGGTTCTGGTTCT
      ------+---------+---------+---------+---------+---------+      180
         LysGlnArgProGlyGlnGlyLeuGluTrpIleGlyAsnIleTyrProGlySerGlySer
      TTTGTTGCAGGCCCAGTTCCAGAGCTCACCTAGCCATTGTAGATAGGCCCAAGACCAAGA
121

ACCAACTACGACGAAAAATTCAAATCTAAAGGCGACCCTCACCGTCGACACCTCTTCTCT
      ------+---------+---------+---------+---------+---------+      240
         ThrAsnTyrAspGluLysPheLysSerLysAlaThrLeuThrValAspThrSerSerSer
      TGGTTGATGCTGCTTTTTAAGTTTAGATTTCCGCTGGGAGTGGCAGCTGTGGAGAAGAAGA
181
```

FIG.2A

```
                   HindIII
     ACCGCGTACATGCAGCTCTCAAGCTTGACCCTCTGAAGACTCAGCTGTTTACTACTGCACC
     ThrAlaTyrMetGlnLeuSerSerLeuThrSerGluAspSerAlaValTyrTyrCysThr     300
241  ----+----+----+----+----+----+----+----+----+----+----+----+
     TGGCGCATGTACGTCGAGAGTTCGAACTGGGAGACTTCTGAGTCGACAAATGATGACGTGG TACTACTACGACTACGAAGGTTTCGCGTACTGGGGTCAAGGTACCCCTCGTTACCGTTTCT
     TyrTyrTyrAspTyrGluGlyPheAlaTyrTrpGlyGlnGlyThrLeuValThrValSer    360
301  ----+----+----+----+----+----+----+----+----+----+----+----+
     ATGATGATGCTGATGCTTCCAAAGCGCATGACCCCAGTTCCATGGGGAGCAATGGCAAGA BamHI
     GCGGATC
     AlaAsp       367
361  ----+--
     CGCctag
```

FIG.2B

```
         NcoI o850                                                        o852
      1  CATGGGACAGGTTCAGCTTCAGCAGTCTAGGACTGAGTTGGGCGAGACCCGGGGCTTCAGT   60
         ----------+---------+---------+---------+---------+---------+
         MetGlyGlnValGlnLeuGlnLeuGlnSerArgThrGluLeuGlyAlaArgProGlyAlaSerVa
         gTACCCTGTCCAAGTCGAAGTCGTCAGATCCTGACTCAACCGCTCTGGGCCCCGAAGTCA
                                                                 o937 o854
     61  GAGGCTGTCCTGCAAGGCTTCTGGATACACCTTCACAACCTTTGGTATAACCTGGGTGAA   120
         ----------+---------+---------+---------+---------+---------+
         lArgLeuSerCysLysAlaSerGlyTyrThrPheThrThrPheGlyIleThrTrpValLy
         CTCCGACAGGACGTTCCGAAGACCTATGTGTGGAAGTGTTGGAAACCATATTGGACCCACTT
                                                  o938

XbaI, o859
    121  GCAGAGAACTGGACAGGGTCTAGAGTGGATTGGAGAAATTTTCCTGGAAATTCGAAGAC   180
         ----------+---------+---------+---------+---------+---------+
         sGlnArgThrGlyGlnGlyLeuGluTrpIleGlyGluIlePheProGlyAsnSerLysTh
         CGTCTCTTGACCTGTCCCAGATCTCACCTAACCTCTTTAAAAGGACCTTTAAGCTTCTG
                                                           o939 o860                                      o861
    181  TTACTACGCTGAGAGGTTCAAGGGCCAAGGCCACACTGACTGCAGACAAATCGTCGACCAC   240
         ----------+---------+---------+---------+---------+---------+
         rTyrTyrAlaGluArgPheLysGlyLysAlaThrLeuThrAlaAspLysSerSerThrTh
         AATGATGCGACTCTCCAAGTTCCCGGTTCCGGTGACTGACGTCTGTTTAGCAGCTGGTG
               o868                                          o867
```

FIG.4A

```
     AGCCTACATGCAGCTCAGCAGCCTGACATCTGAGGACTCCGCGGTCTATTTCTGCGCAAG
     rAlaTyrMetGlnLeuSerSerLeuThrSerGluAspSerAlaValTyrPheCysAlaAr
241  ------+---------+---------+---------+---------+---------+  300
     TCGGATGTACGTCGAGTCGTCGGACTGTAGACTCCTGAGGCGCCAGATAAAGACGCGTTC
                                   o863

AGAGATCCGCTACTGGGGCCAAGGTACCACTCTCACAGTGAGTTCAGCCAAAACAACACC
     gGluIleArgTyrTrpGlyGlnGlyThrThrLeuThrValSerSerAlaLysThrThrPr
301  ------+---------+---------+---------+---------+---------+  360
     TCTCTAGGCGATGACCCCGGTTCCATGGTGAGAGTGTCACTCAAGTCGGTTTTGTTGTGG
                                                            o865

BamHI
     G
     oAsp
361  ----  365
     CCTAG
```

FIG. 4B

```
Control Fusion Protein   2 GVQLQQPGSELVRPGASVKLSCKASGYTFTSYWMHWVKQRPGQGLEWIGN 51  Control Fusion Protein
TSAR-2                   3 QVQLQQSRTELARPGASVRLSCKASGYTFTTFGITWVKQRTGQGLEWIGE 52  TSAR-2

Control Fusion Protein  52 IYPGSGSTNYDEKFKSKATLTVDTSSSTAYMQLSSLTSEDSAVYYCTYYY 101
TSAR-2                  53 IFPGNSKTYYAERFKGKATLTADKSSTTAYMQLSSLTSEDSAVYFCA... 99

Control Fusion Protein 102 DYEGFAYWGQGTLVTVS 118
TSAR-2                 100 ..REIRYWGQGTTLTVS 114
```

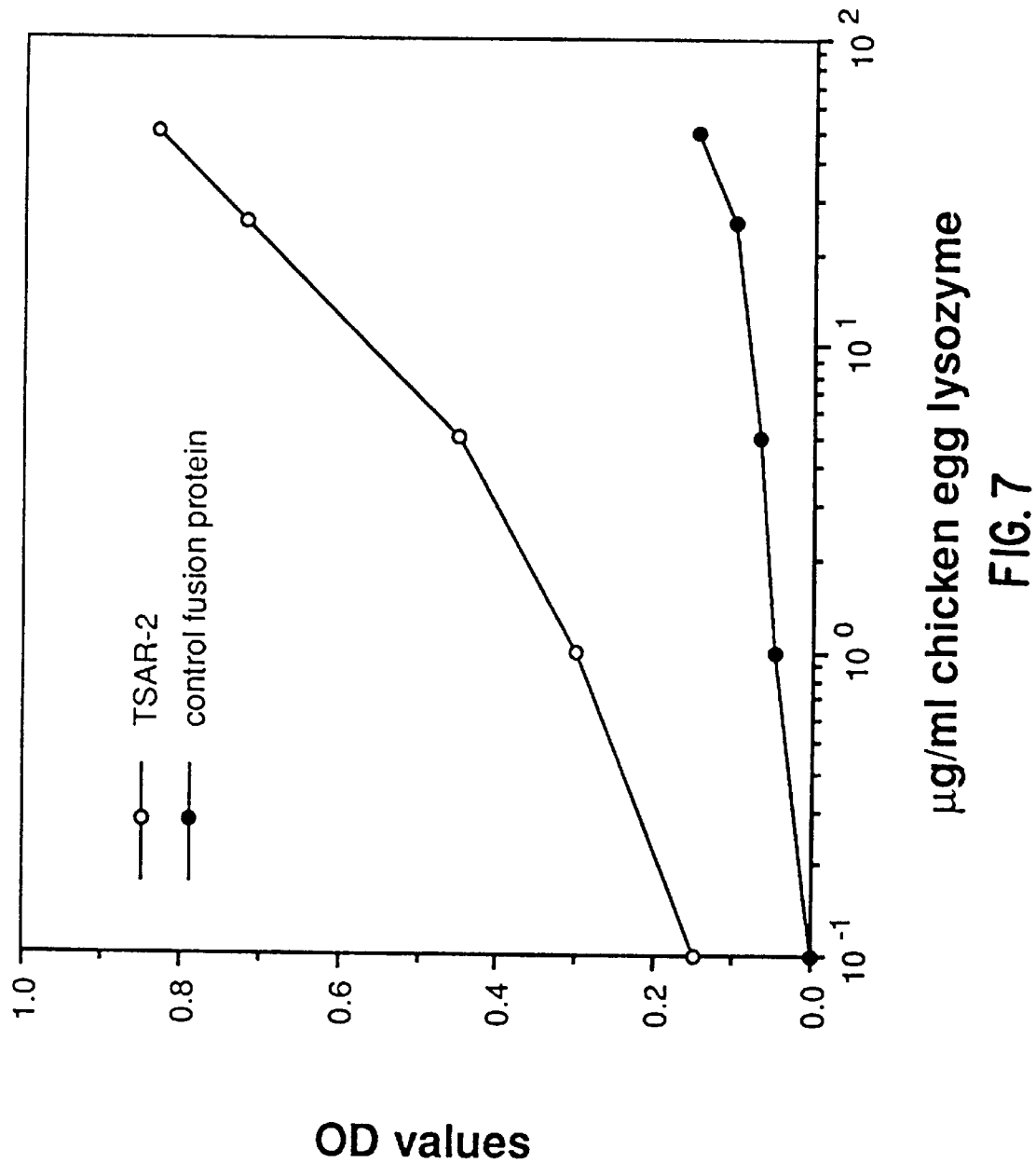

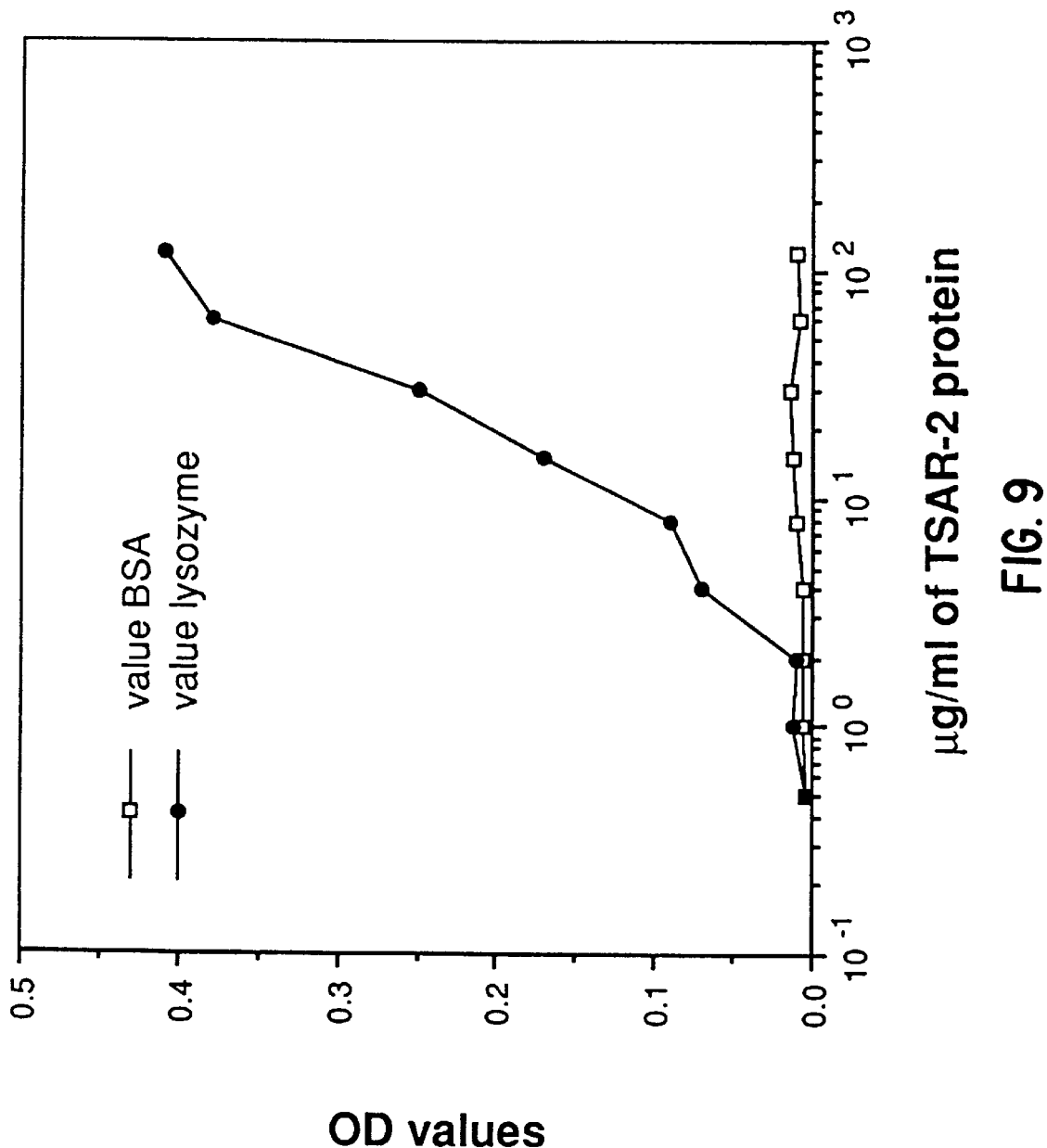

TOTALLY SYNTHETIC AFFINITY REAGENTS

This is a continuation of application Ser. No. 08/022,236, filed Feb. 25, 1993, now abandoned, which is a continuation of application Ser. No. 07/854,133, filed Mar. 19, 1992, now abandoned, which is a continuation of application Ser. No. 07/480,420 filed Feb. 15, 1990, currently abandoned.

TABLE OF CONTENTS
1. Introduction
2. Background
   2.1. Binding Interactions
   2.2. Protein Structural Motifs Involved in Some Known Affinity Reactions
      2.2.1. Regulatory DNA Binding Proteins
      2.2.2. RNA Binding Proteins
      2.2.3. Metal Binding Proteins
      2.2.4. Nucleotide Fold and GTP Binding Proteins
      2.2.5. Calcium Binding Peptides
      2.2.6. Adhesive Proteins
   2.3. Antibody Structures
   2.4. Oligonucleotide Synthesis And Mutagenesis
   2.5. Recombinant DNA Technology and Gene Expression
3. Summary
   3.1. Advantages and Objects of the Invention
   3.2. Definitions and Abbreviations
   3.3. Amino Acid Code
4. Brief Description of the Figures
5. Detailed Description of the Invention
   5.1. TSARs
   5.2. Method To Prepare TSARs
   5.3. Applications and Uses of TSAR
6. Example: Materials and Methods
   6.1. Conditions For Restriction Enzyme Digestion
   6.2. Bacterial Strains and Plasmids
   6.3. Oligonucleotide Assembly
   6.4. DNA Sequencing
7. Example: Construction of an Expression Vector
   7.1. The Initial Vector pJG200
   7.2. Removal of the $P_R, C_{I857}$ Repressor and Amino Terminus of Cro
   7.3. Addition of the PTAC Promoter, Shine Dalgarno Sequence and ATG Codon
   7.4. Improvement of the Ribosome Binding Site
8. Example: Control Fusion Protein and TSAR-1 Construction
9. Example: TSAR-2 Construction
10. Example: Cell Growth and Expression for TSAR Purification
11. Example: Purification of The Control Fusion Protein and TSAR-2
12. Example: Lysozyme Binding Assay of TSAR-2
13. Deposit of Microorganisms

1. INTRODUCTION

The present invention relates to novel reagents and the process for making them. This invention provides a process for synthesizing and identifying new binding reagents of specific affinity. The Totally Synthetic Affinity Reagents (hereinafter TSARS) are concatenated heterofunctional polypeptides or proteins having a binding domain and at least one additional peptide effector domain that is chemically or biologically active. The TSARs can be used as intermediates to form unifunctional polypeptides or proteins having a desired binding activity.

In the invention, DNA encoding a binding domain and DNA encoding an effector domain are inserted into a vector using recombinant DNA technology methods. Following transformation of vectors into cells, expressed proteins are screened for interactions with a ligand of choice to identify TSARs of defined specificity, affinity and avidity. The method of the present invention differs, inter alia, from prior art methods for forming fusion proteins in that the nucleotide sequence encoding a putative binding domain having specificity for a ligand of choice is obtained by a process of mutagenesis as described herein.

A schematic of the general method of the invention follows:

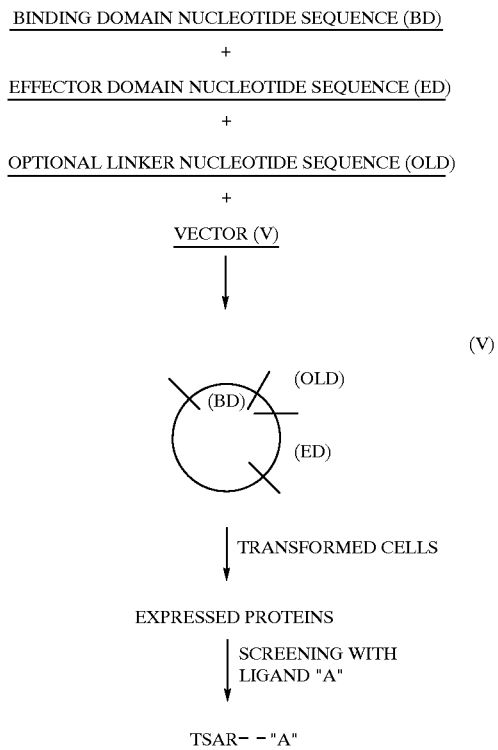

BINDING DOMAIN NUCLEOTIDE SEQUENCE (BD)
+
EFFECTOR DOMAIN NUCLEOTIDE SEQUENCE (ED)
+
OPTIONAL LINKER NUCLEOTIDE SEQUENCE (OLD)
+
VECTOR (V)
↓
(V)

↓ TRANSFORMED CELLS

EXPRESSED PROTEINS
↓ SCREENING WITH LIGAND "A"

TSAR- - "A"

PROTEIN--BINDING DOMAIN/OPTIONAL LINKER/EFFECTOR DOMAIN

In an alternative embodiment, a third nucleotide sequence encoding a linker peptide is inserted between the nucleotide sequences encoding the binding domain and the effector domain. This schematic is provided for illustrative purposes only and is not to be construed as limiting the invention. Other alternative modes will become apparent to those of skill in the art upon reviewing the following description, examples, figures and appended claims.

2. BACKGROUND

2.1. Binding Interactions

The binding of molecules to each other involves direct partner specificity, interaction and stability. The strength of the interaction is determined by the number of atomic bonds that are made and their overall length and strength. In general, bonds between catalytic biomolecules must be reversible because binding partners must be recycled. For example, in enzyme-substrate recognition, binding constants are low so that multiple rapid reactions can occur. Similarly, binding initiation interactions between promoter DNA and RNA polymerase also require less than maximal affinity and stability otherwise the RNA polymerase enzyme is unable to migrate from the promoter and is transcriptionally inactive. Thus, bonds between biological molecules are frequently not of the highest affinity and stability possible although binding reactions of structural and surface components that involve permanent cell-cell interactions and anchorage functions may be very stable with high affinity between the binding partners.

Binding can be accomplished by charge attraction between surfaces and/or by pairing complementary three dimensional molecular surfaces or structures, e.g. a protruding surface fitting into a cavity. The tertiary structure of the protrusion or cavity is the result of flexible polypeptide chains forming shapes that are determined by weak chemical bonds. Thus the amino acid sequence as the primary structure of a peptide provides the chemical subgroups that are aligned in proper position to effectuate proper interactions by the secondary and tertiary structure of the peptide. The types of weak bonds involved in tertiary structure include van der Waals bonds, hydrophobic bonds, hydrogen bonds and ionic bonds. Just as these bonds are involved in intramolecular structure, they can also be involved in intermolecular binding between macromolecules. Thus, intermolecular binding is accomplished by electrostatic bonds, hydrogen bonds, Van der Waals bonds, etc., as well as by combinations thereof. It is difficult to predict which amino acids in a region of a protein structure are responsible for what function, even with the aid of a known tertiary structure. It becomes even more difficult to predict the effect of specified amino acid changes. Predictions of important interacting sequences based on similarities of primary sequence can be incorrect for failure to recognize sequence similarity arising from a common genetic origin rather than from protein design and function constraints. See Subbiah, J. Mol. Biol. 206: 689 (1989). At this point in time it is not only impossible to predict what amino acid changes within a peptide will result in a new or altered protein function, it is also impossible to predict what sequence of amino acids will produce a peptide of given function. Thus, the analysis of known interactions at the molecular and atomic level is completely unsuitable for developing wholly new interactions, especially those that might not occur in nature where macromolecular interactions are limited to the constraints imposed by the aqueous environment within cells and the subsequent requirements of biological and biochemical interactions.

In contrast to the prior art which has not solved the difficulties of developing totally novel binding specificities, the present invention provides a method for producing polypeptides or proteins having a desired binding specificity similar to naturally occurring binding proteins which does not require detailed information with regard to either the specific amino acid sequence or secondary structure of the naturally occurring binding protein. In addition, the method provides a process to generate and identify new peptide compositions having new binding interactions that are not limited to natural interactions or constrained by the evolutionary process.

2.2. Protein Structural Motifs Involved in Some Known Affinity Reactions

The study of known interactions and known components has delineated the minimum size requirements for macromolecular interactions. A significant finding of macromolecular structure and function studies is that interactions involving large macromolecules are often limited to a small region of the macromolecule. Moreover, in some cases similar types of interacting molecules have been shown to have similar structures in comparable regions of interaction. Specificity between individual partners arises then from distinct chemical subgroup and atomic interactions between the molecular partners.

Described below are only a few of the characterized protein structural motifs that are involved in specific binding interactions, especially those of regulatory and developmental significance. A more comprehensive description of structural and functional analyses of characterized solved protein structures can be found in the Bibliographic Files of the Protein Data Bank located at Brookhaven National Laboratory. The binding regions exemplified by each motif described below are small regions of the total protein well within the size range of the binding domains in the present invention. In addition, these motifs suggest that secondary structure similarities are often more important in binding than are specific amino acid sequences. Because secondary structure predictions are hardly accurate, predictions of what amino acids are involved in binding in any given sequence without other independent evidence are impossible.

2.2.1. Regulatory DNA Binding Proteins

Genetic, biochemical, physiological and crystallographic studies of two bacterial phage repressors and the cyclic AMP receptor protein (CAP) lead to the development of the helix-turn-helix protein structural motif for sequence specific DNA binding interactions. The helix-turn-helix structural motifs that contact DNA are similar in each protein although the actual protein sequences vary. Sequence homology studies, while complicated by the evolutionary relatedness of the proteins, suggest that other DNA-binding proteins like lac repressor, lambda cII protein and P22 repressor share the helix-turn-helix motif. Proteins containing helix-turn-helix motifs are reviewed in Pabo and Sauer, Ann. Rev. Biochem. 53: 293 (1984).

More recently, two protein structural motifs other than the helix-turn-helix have been demonstrated in DNA binding proteins. The "leucine zipper" is a periodic repetition of leucine residues at every seventh position over eight helical turns in the enhancer binding protein or EBP of rat liver nuclei [Landschultz et al., Science 240: 1759 (1988)]. Noting that the α helix within this region exhibits amphipathy wherein one side of the helix is composed of hydrophobic amino acids and the other helix side has charged side chains and uncharged polar side chains, the authors proposed that this structure had unusual helical stability and allowed interdigitation or "zippering" of helical protein domains, including both inter- and intra-protein domain interactions.

In 1985, Berg [Science 232: 485 (1986)] noted that five classes of proteins involved in nucleic acid binding and gene regulation could form small, independently structured, metal-binding domains that were termed zinc-fingers. The five classes were 1) the small gag type nucleic acid binding proteins of retroviruses with one copy of the sequence $Cys-X_2-Cys-X_4-His-X_4-Cys$, 2) the adenovirus E1A gene products with $Cys-X_2-Cys-X_{13}-Cys-X_2-Cys$; 3) tRNA synthetases with $Cys-X_2-Cys-X_9-Cys-X_2-Cys$; 4) the large T antigens of SV40 and polyoma viruses of $Cys-X_2-Cys-X_{11-13}-His-X_2-His$; and 5) bacteriophage proteins with $Cys-X_3-His-X_5-Cys-X_2-Cys$, where X is any amino acid. Berg predicted that these sequences were involved in metal binding like the TFIIIA factor of *Xenopus laevis* with Cys-$X_{2-5}$-Cys-$X_{12}$-His-$X_{2-3}$-His [Miller et al., EMBO J. 4: 1609 (1985)] and the Zn domain of aspartate carbamoyltransferase with Cys-$X_4$-Cys-$X_{25}$-Cys-$X_2$-Cys [Honzatko et al., J. Mol. Biol. 160: 219 (1982)]. Such predictions have been borne out.

The helix-turn-helix, zinc-finger and leucine-zipper motifs can be found singly, multiply or as a mixture with other domains in any given protein, e.g., the poly (ADP-ribose) polymerase involved in DNA replication and repair processes has been suggested to contain a zinc finger and a nucleotide binding fold [Cherney et al., Proc. Natl. Acad. Sci. 84: 8370 (1987)].

2.2.2. RNA Binding Proteins

Although not as well characterized as the DNA binding proteins, RNA binding proteins are known. For example, proteins that associate directly with ribosomal RNAs, the RNAs of snRNPs and scRNPs, and with mRNAs all have regions that interact with RNA, and the interaction is often with a specific nucleic acid sequence. Other proteins like T4 gene 32 protein recognize RNA in a non-sequence specific manner. Different methods have been used to identify the specific RNA binding regions of these proteins.

2.2.3. Metal Binding Proteins

In addition to the regulatory Zn metal binding proteins discussed by Berg (supra Section 2.2.1), small, ubiquitous sulfur-rich peptides of approximately 60–100 amino acids, which are called metallothioneins, bind a variety of metal ions and are involved in heavy metal detoxification in vertebrates and fungi [Metallothioneins, pp. 46–92 eds. Kagi and Nordberg, Birkhauser Verlag Basel (1979); Tolman U.S. Pat. No. 4,732,864 issued Mar. 22, 1988].

The term phytochelatin was proposed for the major heavy metal binding peptides of higher plants [Grill et al., Science 230: 674 (1989)]. The structure of these small peptides was determined to be $NH_3^+$-γ Glu-Cys-γGlu-Cys-γGlu-Cys-γ Glu-Cys-Gly-Coo$^-$ with minor components of (γGlu-Cys)$_n$ Gly where n=3, 5, 6 or 7. The peptides were induced by and bound $Cd^{++}$, $Cu^{++}$, $Hg^{++}$, $Pb^{++}$ and $Zn^{++}$.

2.2.4. Nucleotide Fold and GTP Binding Proteins

The crystal structure of the GDP-binding protein EF-Tu was determined [Jurnak, Science 230: 32 (1985); la Cour et al., EMBO J. 4: 2385 (1985)] and indicated that a region of twisted β sheet was involved in nucleotide binding. The nucleotide sits in a cavity at the carboxy ends of the β-sheet with contacts to the protein situated in four loops connecting β-strands with α-helices. The folding pattern around the diphosphate component and the residues binding the nucleotide are highly conserved between bacteria and other species [McCormick et al., Science 230: 78 (1985)]. Constant features were a loop connecting a β-strand at the carboxy edge of a β-sheet with an antiparallel helix as seen in the Rossman dinucleotide fold [Rao and Rossmann, J. Mol. Biol. 76: 241 (1973)]. The loop in EF-Tu was eight amino acids long and the Gly-$X_4$-Gly-Lys sequence showed conservation with other purine-nucleotide binding proteins. The guanine base binding portion of the loop of sequence Asn-Lys-Cys-Asp was also conserved.

2.2.5. Calcium Binding Peptides

The conserved EF-hand motif or helix-loop-helix structure for $Ca^{++}$ binding consists of a twelve amino acid loop with alternating amino acids having anionic or electronegative groups in their side chains to form an octahedral coordinate complex with the $Ca^{++}$ ion that is flanked by two amphipathical a helical segments [Kretsinger and Nickolds, J. Biol. Chem. 248: 3313 (1973)].

Crystallin is a $Ca^{++}$ binding protein wherein a fifty amino acid region of the protein between residues 300 and 350 possess the EF-hand motif characterized for $Ca^{++}$ binding [Sharma et al., J. Biol. Chem. 264: 12794 (1989)].

2.2.6. Adhesive Proteins

Proteins that are present in extracellular matrices and in body fluids are involved in the attachment of cells to their surrounding matrices and other cells. The adhesive qualities of proteins known as integrins such as fibronectin, vitronectin, osteopontin, collagens, thrombospondin, fibrinogen and von Willebrand factor are dependent on the tripeptide motif Arg-Gly-Asp which functions as their cell recognition site. Ruoslahti and Pierschbacher, Cell 44: 517 (1986). Affinity chromatography using Sepharose covalently coupled to purified adhesin protein allowed the isolation of cell surface receptor proteins specific for the bound adhesin. Pytela et. al. Cell 40: 191 (1985); Pytela et. al. Science 231: 1559 (1986). Although a search of the protein sequence database revealed 183 Arg-Gly-Asp sequences, not all of the proteins containing the motif are recognized as a cell surface adhesive protein, suggesting that factors other than the primary sequence of a small region must be considered in defining a binding site.

The role of the tripeptide Arg-Gly-Asp recognition site in cell adhesion, migration, and differentiation has been recently reviewed. See Ruoslahti and Pierschbacher, Science 238: 491 (1987). However, a different binding site was identified in laminin that consisted of the amino acid sequence Cys-Asp-Pro-Gly-Tyr-Ile-Gly-Ser-Arg. Graf et. al., Cell 48: 989 (1987).

2.3. Antibody Structures

Antibodies are composed of four peptide chains linked by sulfhydryl bridges and include two identical large heavy (H) chains and two smaller light (L) chains. Antibodies have a Y structure composed of three major regions: the Fv antigen binding site of the H and L chains on each of the upper tips of the Y, the Fab region composed of the upper Y arms and the Fc area of the Y stalk.

Sequence comparisons of light and heavy chains reveal that both contain variable (V) and constant (C) regions. Within each variable region are found complementarity determining regions (CDRs) which contribute binding specificity to numerous different antigens by the hypervariability of their sequence.

Cells synthesizing antibodies undergo DNA rearrangements by recombination of different variable, D, and J sequences at two steps in antibody maturation. One set of rearrangements occurs in the genomic DNA and another in mature B-cell mRNA to produce a large and diverse number of possible sequence combinations that result in a conservative approximation of $10^6$–$10^8$ possible individual antibody molecules. See Harlow and Lane, Antibodies: A Laboratory Manual, Cold Spring Harbor Laboratory (1988) pages 1–52, for a more detailed description of immunochemical methods, introductory discussions of key features of the immune response, structures of the different classes of antibody molecules, and the mechanism of the antibody response.

Antibodies are defined in terms of affinity, which is strength of binding, and avidity, which is a more complicated estimate of the stability or functional affinity of the binding reaction. Although combinations of various chromosomal V, D and J regions allow diversity of antibodies and generate widely varying affinities and avidities to different molecules, that diversity is limited by what can be recombined in vivo, by self recognition limitations, by the inherent limitations of the aqueous environment within living cells, by the nature of the antigen itself, i.e. a toxic compound may be lethal before it is antigenic, and by the inherent limitations of cell—cell interactions that are involved in antibody synthesis.

Limitations are also apparent in the quantity, quality and purity of antibody that can be produced by an animal. Although monoclonal antibody production does overcome some of these limitations, it does not surmount many of them. Moreover, monoclonal antibodies are still limited to those antibody sequences produced in vivo. The production of monoclonal antibodies produced by fusion and growth of animal cells in vitro still require costly and technical manipulations that limit their usefulness and are dependent on cells for the expression of complete molecules. Thus severe limitations are apparent in the ability to produce and grow appropriate clones of B-cells producing the desired antibody of desired specificity, affinity and avidity.

Immunoglobulins possess inherent characteristics which also reduce their usefulness. The presence or absence of an antibody generally cannot be directly measured because, with the exception of antibodies specific for transition state analogs of enzymatically catalyzed reactions, an antibody has no catalytic activity that can be assayed. One of the present limitations to the use of monoclonal antibodies is the ability to detect an antibody bound to an antigen. The presence of antibodies per se must be measured indirectly usually with another antibody that has a covalently linked reporter group such as an enzyme or a radioactive probe. Therefore indirect means of quantitation are required for applications using antibodies, necessitating multiple technical steps for measurement with each step having its own hazards and inconveniences which include the need for technical expertise in personnel, the use of multiple and often labile or hazardous reagents, time consumption and costs. Furthermore the precision and quantitation in these indirect tests is inherently limited to the efficiency and kinetics of the indirect probe's association with the antibody which can negatively impact on the antibody-antigen interaction of interest which affects the accuracy and reliability of the results.

Attempts have been made to overcome these limitations. Recombinant DNA technology has allowed the production of large amounts of monoclonal antibody chains in cell culture [Cabilly et al., Proc. Nat'l. Acad. Sci. 81: 3273 (1988); Guarente et al., Cell 20: 543 (1980)]. Of course the production of any such antibody by recombinant DNA technology requires specific engineering using known DNA sequences for each and every recombinant monoclonal antibody desired. That process requires elaborate, time consuming, costly and complex steps of identification, isolation, sequencing and manipulation of the specific antibody gene of interest so that large amounts of that antibody or a chimeric molecule containing a portion of that antibody can be genetically engineered.

Recombinant molecules containing constant portions of the antibody identical to those of the host species have been engineered for therapeutic purposes. Natural production of host antibodies is largely infeasible and impractical since human experimental subjects producing the desired antibody are not available except in rare cases and hybridoma production with human cell fusions has been generally unsuccessful. Recombinant chimeric antibodies have been produced in an attempt to solve these difficulties. See e_.g. Morrison et al., Proc. Nat'l. Acad. Sci. 81: 6851 (1984); Jones et al., Nature 321: 522 (1986).

Antibody binding specificity is determined primarily by the loops at tips of β-sheet defined by the variable domains of the H and L chains found in Fv and Fab proteolytic fragments. Recently recombinant DNA techniques have been used to engineer Fv fragments with the antigen binding loops of mouse anti-lysozyme D1.3 antibody, the variable domains of H human NEW chains and L human REI chains [Riechmann et al., J. Mol. Biol. 203: 825 (1988)]. The two H and L chains assembled in vivo and a functional Fv fragment could be isolated. 2.4. Oligonucleotide Synthesis and Mutagenesis The ability to chemically synthesize DNA allowed scientists the opportunity to develop mutations at any base in a given nucleic acid sequence. The technique overcame the obstacles presented by in vivo mutagenesis techniques such as diploidy, genome complexity, lack of suitable selection schemes, high toxicity to the scientist caused by the mutagen and low frequency of occurrence.

Recombinant DNA technology provided methods of easily deleting large blocks of sequence by juxtaposing otherwise separated restriction enzyme sites within a sequence to crudely map regions of interest. Chemical mutagenesis is useful but is limited in scope to alteration of the nucleotides that are affected by the chemical, i.e., C to T transitions produced by sodium bisulfite. Oligonucleotide site specific mutagenesis allows mutations of a specific nucleotide by construction of a mutated oligonucleotide that includes modifications at the site of interest. Ramdom mutagenesis techniques allow the rapid and easy generation of a large number of a variety of uncharacterized mutations.

Matteucci and Heyneker [Nucl. Acids Res. 11 3113 (1983)] used what they termed "ambiguous synthesis" to mutagenize a 9 bp sequence preceding the initiation codon for bovine growth hormone. Their goal was to develop a ribosomal binding site that maximally optimized translational expression of the protein. In their method, oligonucleotides were manually synthesized on a cellulose support using monomer addition triester chemistry. During synthesis, the three precursors not specified by the starting sequence were present at 8% while the specified sequence precursor was present at 75% allowing ambiguous incorporation of precursor at a predictable frequency at each cycle of synthesis. The ambiguous oligos were added to a specially prepared vector that had been engineered to have appropriate restriction sites adjacent to the ATG start codon. The ambiguous oligonucleotides were ligated to the vectors, transformed and screened for nonhomology to the wild type starting sequence. DNAs containing nonhomologous sequences were sequenced to obtain frequency data. The cells containing the ambiguously synthesized oligonucleotides were screened for bovine growth hormone production to identify up and down expression mutations.

Wells et. al. [Gene 34 : 315 (1985)] developed a method of specific codon mutation to generate nineteen amino acid substitutions at the single codon position 222 of subtilisin. Different oligonucleotide pools were synthesized and ligated into the vector and the DNAs from different colonies were sequenced. Desired mutants were then transformed into *B. subtilis* to produce secreted mutant subtilisin.

McNeil and Smith [Mol. Cell. Biol. 5 : 3545 (1985)] used double stranded mutagenesis to develop random variations of a 7 bp sequence in the CYC1 transcriptional start site region. They utilized a mixture of 71% of the specified precursor defined by the wild type sequence and doped the precursor reservoir with 9.7% of each of the other precursors in order to generate double mutations over the 7 bp sequence. They also developed a binomial distribution equation giving nucleotide substitution yields of 9, 26 and 32% for 0, 1 and 2 nucleotide sequence alterations within the target site.

Oliphant et. al [Gene 44 : 177 (1986)] described a method for cloning random or highly degenerate nucleotide sequences following chemical automated synthesis of oligonucleotides. The capping reaction reagent normally added after each step was deleted allowing increased yield by including oligonucleotide that failed to react in the previous step. Heterogeneous oligonucleotide lengths were a second result of the omission of the capping step. The oligonucleotides were cloned directly or after incubation with Klenow fragment to convert them to double stranded form. After sequencing, the nucleotide and dinucleotide frequency's of 26 random insertions were determined, thus demonstrating the utility of the mutagenic technique.

Hutchinson et al. [Proc. Nat'l. Acad. Sci. 83 : 710 (1986)] developed a complete library of point substitution mutations in a thirty nucleotide region of the glucocorticoid response element of mouse mammary tumor virus. Mutations were generated by contaminating each of the four precursor reservoirs of an automated DNA synthesizer with small concentrations of the three other precursors to produce a 5% total impurity containing 1.5% of each of the other three precursors. The oligonucleotides were cloned into M13mp11 to screen for the generation of termination codons which occurred in about 10% of transformants. The sequences of 546 random plaques indicated that mutations were present at each of the thirty nucleotides. Eighty-eight of the possible ninety substitution mutations were found, as were fourteen single base insertions and six single base deletions. Seventy-four of the eighty-eight substitutions were recovered as single mutations. A statistical analysis of the number of transformants that needed to be sequenced to give a probability of a complete library of single or double mutations was included.

Derbyshire et al. [Gene 46 : 145 (1986)] described an automated method of producing and cloning single stranded oligonucleotides that direct a specific change at a chosen site of a fragment of known DNA sequence. A mixed sequence 28 mer preparation was made by contaminating each of the monomer reservoirs with each of the other precursors at 1.54 the concentration of the wild type precursor monomer. The authors used a probability equation that predicts the probability of mutations for any length of oligo using a wide range of relative concentrations of mutant and wild type precursor monomers. The observed yield of mutations for single mutations (23), double mutations (8), triple mutations (4) and quadruple mutations (1) as compared to wild type sequence (18) correlated remarkably well with the yield predicted by the equation.

The use of random mutagenesis over a broad target of the 5' end of the VA I gene was used to identify areas of particular interest and function. Snouwaert et al. [Nucl. Acids Res. 15: 8293 (1987)] generated libraries containing randomly dispersed and clustered point mutations of the adenovirus VA I gene by contaminating each of the precursor phosphoramidite solutions with 2.5% of the other phosphoramidites during oligonucleotide synthesis of segments of the VA I gene. Following assembly of the constituent oligonucleotides, the mutagenized oligonucleotide library corresponding to the 5' end of the VA I gene was cloned into an M13 vector. Individual clones were then sequenced by the chain termination method and used to reassemble a whole VA I gene. Each reassembled, sequenced, and mutated VA I gene was transcribed in vitro to test the effect of random mutations on the transcriptional efficiency of the VA I gene. A second round of clustered mutagenesis then aided in identifying the function of particular nucleotides within a limited region.

2.5. Recombinant DNA Technology and Gene Expression

Recombinant DNA technology involves insertion of specific DNA sequences into a DNA vehicle (vector) to form a recombinant DNA molecule which is capable of replication in a host cell. Generally, the inserted DNA sequence is foreign to the recipient DNA vehicle, i.e., the inserted DNA sequence and the DNA vector are derived from organisms which do not exchange genetic information in nature, or the inserted DNA sequence may be wholly or partially synthetically made. Several general methods have been developed which enable construction of recombinant DNA molecules.

Regardless of the method used for construction, the recombinant DNA molecule must be compatible with the host cell, i.e., capable of autonomous replication in the host cell or stably integrated into one or more of the host cell's chromosomes. The recombinant DNA molecule should preferably also have a marker function which allows the selection of the desired recombinant DNA molecule(s). In addition, if all of the proper replication, transcription, and translation signals are correctly arranged on the recombinant vector, the foreign DNA will be properly expressed in, e.g., the transformed bacterial cells, in the case of bacterial expression plasmids, or in permissive cell lines or hosts infected with a recombinant virus or carrying a recombinant plasmid having the appropriate origin of replication.

Different genetic signals and processing events control levels of gene expression such as DNA transcription and messenger RNA (mRNA) translation. Transcription of DNA is dependent upon the presence of a promoter, which is a DNA sequence that directs the binding of RNA polymerase and thereby promotes mRNA synthesis. The DNA sequences of eukaryotic promoters differ from those of procaryotic promoters. Furthermore, eukaryotic promoters and accompanying genetic signals may not be recognized in or may not function in a procaryotic system and conversely procaryotic promoters are not recognized and do not function in eukaryotic cells.

Similarly, translation of mRNA in procaryotes depends upon the presence of the proper procaryotic signals, which differ from those of eucaryotes. Efficient translation of mRNA in procaryotes requires a ribosome binding site called the Shine-Dalgarno (S/D) sequence on the mRNA [Shine, J. and Dalgarno, L., Nature 254:34 (1975)]. This sequence is a short nucleotide sequence of mRNA that is located before the start codon, usually AUG, which encodes the amino-terminal methionine of the protein. The S/D sequences are complementary to the 3' end of the 16S rRNA (ribosomal RNA), and probably promote binding of mRNA to ribosomes by duplexing with the rRNA to allow correct positioning of the ribosome.

Although the Shine/Dalgarno sequence, consisting of the few nucleotides of complementarity between the 16S ribosomal RNA and mRNA, has been identified as an important feature of the ribosome binding site [Shine and Dalgarno, Nature 254: 34 (1975); Steitz, in Ribosomes: Structure, Function and Genetics ed. Chambliss et al. Baltimore, Md., University Park Press pp. 479–495 (1980)], computer analysis has indicated that approximately one hundred nucleotides surrounding the AUG initiating codon are involved in ribosome/mRNA interaction as indicated by proper prediction of translation start signals [Stormer et al., Nucl. Acids Res. 10:2971 (1982); Gold et al., Proc. Natl. Acad. Sci. 81:7061 (1984)]. As of yet, no accurate prediction of what actually provides the best and complete ribosome binding site for maximum translation of a specific protein has been made [see Joyce et al., Proc. Natl. Acad. Sci. 80:1830 (1983)].

Schoner and Schoner recognized the significance of the entire ribosome/mRNA interaction region in the development of recombinant expression vectors in their characterization of a 72 bp sequence termed the "minicistron" sequence [see Figure 1 of Schoner et al., Proc. Natl. Acad. Sci. USA 83: 8506 (1986)]. A one base deletion in the first cistron of the "minicistron" sequence was sufficient to increase the production of the downstream recombinant protein Met-[Ala]bGH from 0.4% to 24% of total cell protein (See Figure 4, pCZ143 compared to pCZ145, Schoner et al., id.).

Alternatively a two base insertion also resulted in significant expression of the peptide encoded by the second cistron. Experiments indicated that the differences in expression were due to translational differences because mRNA levels in these constructs were essentially equivalent (no more than 3 fold different) as compared to the expressed protein differences (which were approximately 50 fold). The conclusion was that the position of the stop codon that terminates translation of the first cistron of the minicistron sequence affected the efficiency of translation of the second cistron containing the coding sequence of the recombinant protein. Most importantly Schoner & Schoner's work indicated that one or two base changes in the sequence immediately preceding the coding sequence of a recombinant protein can have tremendous effects on downstream expression.

Successful expression of a cloned gene requires sufficient transcription of DNA, translation of the mRNA and in some instances, post-translational modification of the protein. Expression vectors have been used to express proteins under the control of an active promoter in a suitable host, and to increase protein production.

3. SUMMARY

The present invention relates to novel reagents and the process for making them. This invention provides a process for synthesizing and identifying new binding reagents of specific affinity. The Totally Synthetic Affinity Reagents (TSARs) are concatenated heterofunctional polypeptides or proteins in which at least two functional groups are brought together in a single peptide chain: a binding domain and an additional effector domain that is chemically or biologically active. The polypeptides or proteins are expressed in prokaryotic or eukaryotic cells as hybrid fusion proteins comprising at least one binding domain, with affinity for a ligand, linked to one or more additional chemically or biologically active effector domains. The chemically or biologically active effector domain can include peptide moieties such as an enzyme or fragment thereof, a toxin or fragment thereof, a therapeutic agent, a peptide that is useful for detection, a peptide that enhances expression of the TSAR molecule, or a peptide whose function is to provide a site for attachment of a substance that is useful for detection. The binding domain can be separated from the effector domain that is biologically or chemically active by a linker peptide domain. If desired, the linker domain can be either stable or susceptible to cleavage either enzymatically or chemically.

The invention provides a novel method for producing heterofunctional binding fusion protein molecules, termed TSARs, comprising the steps of: (a) inserting (i) a first nucleotide sequence encoding a putative binding domain having specificity for a ligand of choice and (ii) a second nucleotide sequence encoding a biologically or chemically active polypeptide or protein effector domain into a vector downstream from a 5'ATG start codon to produce a library of vectors coding for an in-frame fusion protein; (b) transforming cells with the vectors formed in step (a) to express the fusion proteins; and (c) screening the expressed fusion proteins to identify a TSAR having binding specificity for the ligand of choice and the desired second biological or chemical activity, in which the first nucleotide sequence is obtained by a process of mutagenesis.

Mutagenesis, as used in this application, is intended to encompass any process which leads to the production of an alteration, including a deletion, an addition and a substitution of a nucleotide(s), in a sequence of nucleotides encoding a protein, polypeptide or peptide moiety. Hence, mutagenesis can be accomplished by chemical synthesis of an altered nucleotide sequence; by alteration induced in vitro or in vivo by any known mutagen such as ionizing radiation or a chemical mutagenic agent; and by insertion of an altered sequence generated using recombinant DNA techniques such as insertion of isolated genomic DNA, cDNA or a chemically synthesized oligonucleotide sequence. Thus, mutagenesis encompasses random, site directed or site selective techniques known to those of skill in the art.

According to one embodiment of the invention, step (a) of the method further comprises inserting a third nucleotide sequence encoding a peptide linker domain between the first and second nucleotide sequences. The linker domain can be either stable or susceptible to cleavage by enzymatic or chemical reagents. According to one mode of this embodiment, when there is a binding domain and the linker domain is cleavable, the heterofunctional TSAR can be used as an intermediate to prepare a unifunctional binding polypeptide or protein having specificity for a ligand of choice.

According to the present invention, the first nucleotide sequence encoding a putative binding domain comprises a member of a group of sequences of nucleotides obtained by a process of mutagenesis of the nucleotide sequence encoding the binding domain of a receptor or anti-ligand for a ligand of choice. A receptor is selected from the group of naturally occurring receptors such as the variable region of an antibody, an enzyme/substrate or enzyme/co-factor binding site, a regulatory DNA binding protein, an RNA binding protein, a metal binding protein, an integrin or other adhesive protein, a calcium binding protein, a lectin, etc. The nucleotide sequence encoding the binding domain of the receptor is mutagenized, using either random, site directed or site selective techniques known to those of skill in the art, and the resulting group of nucleotide sequences are inserted as the first nucleotide sequence in step (a) of the method of the invention.

According to an alternative method of the present invention using random mutagenesis, the first nucleotide sequence comprises a group of nucleotide sequences generated by random chemical synthesis or assembly of DNA fragments selected by size but not sequence. In this embodiment, randomly generated nucleotide sequences are employed as the first nucleotide sequence in step (a) of the method of the invention to form a library of vectors expressing fusion proteins. The fusion proteins are screened using a ligand of choice to identify a TSAR having binding specificity for the chosen ligand. Using this embodiment of the present invention, the TSAR formed may have rather low binding specificity for the ligand. In such case, the nucleotide sequence encoding the binding domain of the identified TSAR is determined. The determined nucleotide sequence is then mutagenized and steps (a)–(c) of the method of the invention are repeated to identify an additional TSAR having enhanced binding affinity for the chosen ligand. Random mutagenesis, as used in this application, is intended to encompass mutagenesis accomplished either by random chemical synthesis of a nucleotide sequence or by random alteration by any mutagenic agent or by assembly of DNA fragments selected by size but not sequence.

Additionally, the invention includes a unifunctional polypeptide or protein having specificity for a ligand of choice that can be prepared by chemically synthesizing the amino acid sequence of the binding domain of a fusion protein produced according to the method of the invention.

The present invention thus provides novel and improved binding reagents of desired binding specificity and avidity as well as methods for using such reagents for a variety of in vitro and in vivo applications.

3.1. Advantages and Objects of the Invention

The present invention provides a method for forming a binding molecule that is reproducible, quick, simple, efficient and relatively inexpensive. More particularly, the invention provides a method of generating and screening a large library of diverse heterofunctional molecules. Thus, the invention provides a rapid and easy way of producing a large library that results in a family of related peptides with novel and improved binding specificities, affinities and stabilities for a given ligand. The diversity of binding characteristics that can be obtained with the present invention is much greater than the diversity that can be obtained for other binding molecules that are formed in vivo.

In contrast to the prior art that relies on isolation of specific genes and known sequences, the present invention has the advantage that there is no need for purifying or isolating genes nor any need for detailed knowledge of the function of portions of the binding sequence or the amino acids that are involved in ligand binding in order to produce a TSAR. The only requirement is having the ligand needed to screen a TSAR library to find TSARs with affinity for that ligand. Since TSARs are screened in vitro, the solvent requirements involved in TSAR/ligand interactions are not limited to aqueous solvents; thus, nonaqueous binding interactions and conditions different from those found in vivo can be exploited.

TSARs are particularly useful in systems in which development of binding affinities for a new substance and developing different binding affinities for known substances are important factors.

TSARs may be used in any in vivo or in vitro application that might make use of a peptide or polypeptide with binding affinity such as a cell surface receptor, a viral receptor, an enzyme, a lectin, an integrin, an adhesin, a $Ca^{++}$ binding protein, a metal binding protein, DNA or RNA binding proteins, immunoglobulins, vitamin cofactors, peptides that recognize any bioorganic or inorganic compound, etc.

By virtue of the affinity of the binding domain for a target, TSARs used in vivo can deliver a chemically or biologically active effector peptide moiety, such as a peptide, toxin or fragment thereof, or enzyme or fragment thereof, to the specific target in or on the cell. The TSARs can also have a utility similar to monoclonal antibodies or other specific binding molecules for the detection, quantitation, separation or purification of other molecules. In one embodiment, there may exist multiple binding domains that have the same specificity but are fused to another distinct effector polypeptide or protein domain that has a biological or chemical activity. In yet another embodiment, the binding domain is separated from the biologically or chemically active effector polypeptide or protein portion by a linker domain. If the linker is susceptible to chemical or enzymatic cleavage, the TSAR can function as an intermediate in the generation of unifunctional peptides of defined specificity, affinity and stability.

The TSARs that are produced in this invention can replace the function of macromolecules such as monoclonal or polyclonal antibodies and thereby circumvent the need for complex hybridoma formation or in vivo antibody production. Moreover, TSARs differ from other natural binding molecules in that TSARs have an easily characterized and designed activity that can allow their direct and rapid detection in a screening process.

These and other objects, aspects and advantages of the present invention will become apparent to those skilled in the art upon reviewing the following description, examples, figures and appended claims.

3.2. Definitions and Abbreviations

Affinity : Strength of binding

ATG : The DNA codon for f-met and initiation of translation

Avidity : Stability of binding

BSA : Bovine serum albumin

ATCC : American Type Culture Collection bp : Base pair

Kb : Kilobase

ELISA : Enzyme linked immunosorbent assay

HPLC : High pressure liquid chromatography

IPTG : Isopropyl-β-D-thiogalactopyranoside

IgG,M, etc. : Immunoglobulin G, M, etc.

Ligand : A molecule or portion thereof for which a receptor naturally exists or can be prepared LB : Luria Broth mRNA : messenger RNA ONPG : O-nitrophenyl-β-D-galactopyranoside O : oligonucleotide PAGE : Polyacrylamide gel electrophoresis PMSF : phenylmethane sulfonyl fluoride $P_L, P_R$: Promoter left, promoter right of λ phage $P_{TAC}, P_{TRC}$ : Hybrid tryp-lac promoter Receptor : an anti-ligand; any macromolecular compound or composition capable of binding to a particular spatial and/or polar organization of a molecule or portion thereof RNase : Ribonuclease SDS : Sodium dodecyl sulfate X-gal : 5-bromo-4-chloro-3-indolyl-β-D-galactopyranoside YT : Yeast tryptone broth
TBS : Tris Buffered Saline

3.3. Amino Acid Code

Alanine : A, Ala
Arginine : R, Arg
Asparagine N, Asn
Aspartic acid : D, Asp
Cysteine : C, Cys
Glutamic acid : E, Glu
Glutamine : Q, Gln
Glycine : G, Gly
Histidine : H, His
Isoleucine : I, Ile
Leucine : L, Leu
Lysine : K, Lys
Methionine : M, Met
Phenylalanine : F, Phe
Proline : P, Pro
Serine S, Ser
Threonine : T, Thr
Tryptophan : W, Trp
Tyrosine : Y, Tyr
Valine : V, Val

4. BRIEF DESCRIPTION OF THE FIGURES

FIG. 2 depicts the oligonucleotide sequence used in construction of the amino terminal end of the control fusion protein.

FIG. 4 depicts the nucleotide and amino acid sequence of the TSAR-2 binding domain.

FIG. 6 depicts the alignment of the amino terminal end of the control fusion protein with the TSAR-2 binding domain.

FIG. 7 shows the binding of lysozyme to the control fusion protein and TSAR-2.

FIG. 9 illustrates the specificity of TSAR-2 for lysozyme and shows binding of TSAR-2 to lysozyme and bovine serum albumen (BSA). The binding is detected using an assay for β-galactosidase which is the peptide encoded by the effector domain.

5. DETAILED DESCRIPTION OF THE INVENTION

5.1. TSARs

Figure 1:
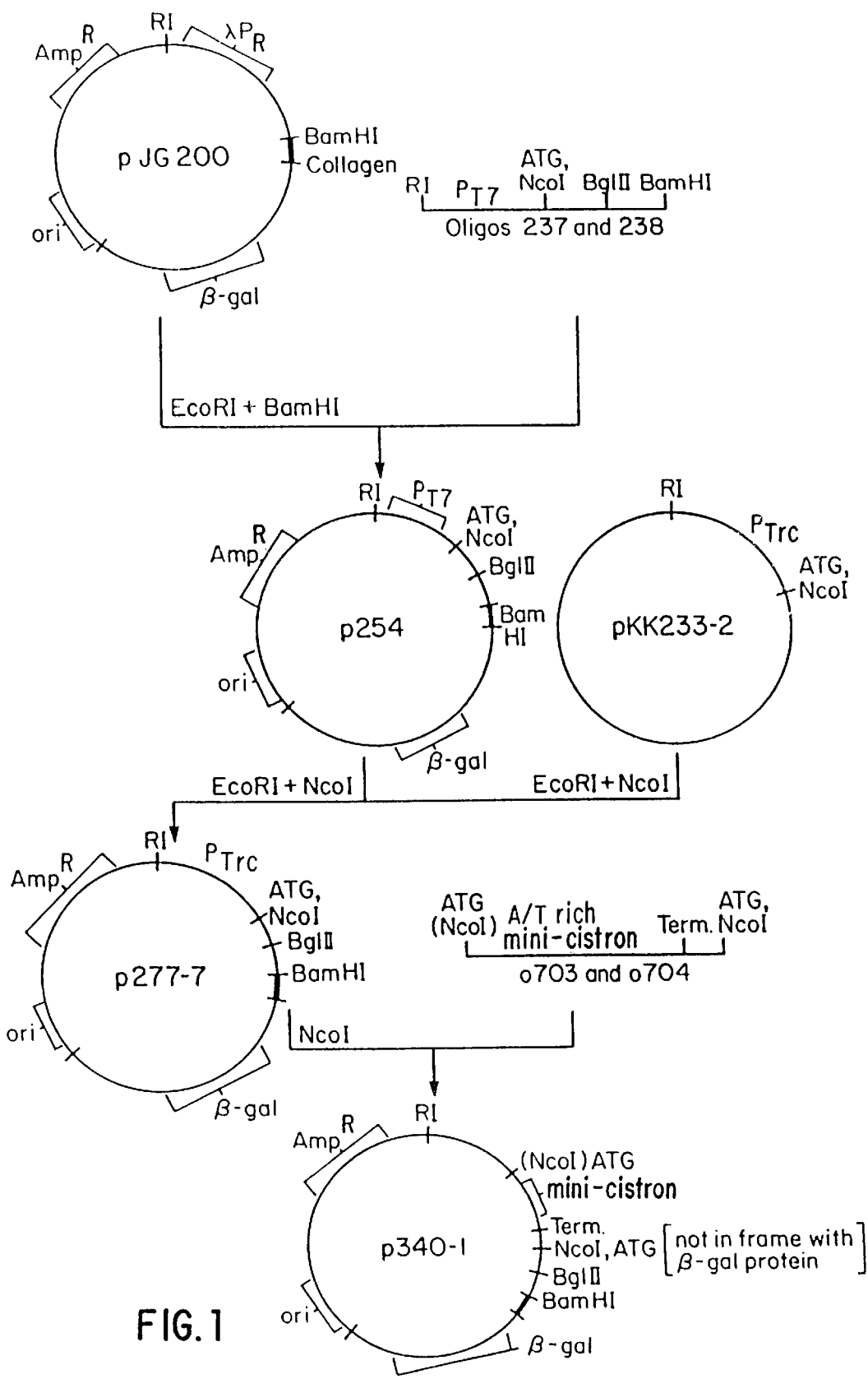
FIG. 1 depicts the steps in construction of the expression vector p340.

In the present invention, novel reagents called TSARs are created and produced as soluble, easily purified proteins that can be made and isolated in commercial quantities. These reagents are concatenated heterofunctional polypeptides or proteins that include at least two distinct functional regions. One region of the heterofunctional molecule is a binding domain with affinity for a ligand that is characterized by 1) its strength of binding under specific conditions, 2) the stability of its binding under specific conditions, and 3) its selective specificity for the chosen ligand. The second peptide portion of the heterofunctional TSAR molecule is an effector domain that is biologically or chemically active such as an enzyme or fragment thereof, a toxin or fragment thereof, a therapeutic agent or a peptide whose function is to provide a site for attachment of a substance such as a metal ion, etc., that is useful for detection. According to one embodiment of the invention, a TSAR can contain an optional additional region, i.e., a linker domain between the binding domain and the effector domain. Linkers can be chosen that allow biological, physical or chemical cleavage and separation of the TSAR regions. TSARs having a cleavable linker portion, thus, can serve as intermediates in the production of unifunctional polypeptides or proteins having a binding function and specificity for a ligand of choice. Alternatively, the linker portion can be stable or impervious to chemical and/or enzymatic cleavage and serve as a link between the binding domain and the other peptide portion(s) of the TSAR.

According to another embodiment of the invention, the TSAR can include multiple binding domains or multiple active effector portions or combinations of multiples of each. The size of a binding domain is not limited, nor is the binding quality of the TSAR limited to a single peptide chain. Monomers, dimers and oligomers of a TSAR protein may singly or in combination affect interaction with the ligand.

In the present invention, a ligand is intended to encompass a substance, including a molecule or portion thereof, for which a proteinaceous receptor naturally exists or can be prepared according to the method of the invention. A receptor is an anti-ligand and includes any macromolecular compound or composition capable of binding to a particular spatial and/or polar organization of a ligand. Thus in this invention, a ligand is a substance that specifically interacts with the binding domain of a TSAR and includes, but is not limited to, a chemical group, an ion, a metal, a peptide or any portion of a peptide, a nucleic acid or any portion of a nucleic acid, a sugar, a carbohydrate or carbohydrate polymer, a lipid, a fatty acid, a viral particle or portion thereof, a membrane vesicle or portion thereof, a cell wall component, a synthetic organic compound, a bioorganic compound and an inorganic compound.

The chemically or biologically active domain of the TSAR imparts detectable, diagnostic, enzymatic or therapeutic characteristics to the TSAR. There is no intended specified order for the two or more regions of the TSAR relative to each other except that the linker domain, if present, must be between the binding domain and the effector domain of the TSAR. The positions of the regions of the TSAR are otherwise interchangeable.

In a particular embodiment, the binding and effector regions of the TSAR protein are separated by a peptide linker domain. The presence or absence of the peptide linker domain is optional as is the type of linker that may be used. The sequence can be stable or it can be susceptible to cleavage by chemical, biological, physical or enzymatic means. If a cleavable linker is used, the sequence employed is one that allows the binding domain portion of the TSAR to be released from the effector domain of the TSAR protein. Thus when a linker is used that is susceptible to cleavage, the heterofunctional TSAR protein can be an intermediate in the production of a unifunctional binding protein, polypeptide or peptide.

In a particular embodiment, the cleavable sequence is one that is enzymatically degradable. A collagenase susceptible sequence is but one example (see, for example, Sections 8 and 9, infra). Other useful sequences that can be used as an enzymatically cleavable linker domain are those which are susceptible to enterokinase or Factor Xa cleavage. For example, enterokinase cleaves after the lysine in the sequence Asp-Asp-Asp-Lys. Factor Xa is specific to a site having the sequence Ile-Glu-Gly-Arg, and cleaves after arginine. Another useful sequence is Leu-Val-Pro-Arg-Gly-Ser-Pro which is cleaved by thrombin between the Arg and Gly residues. Other enzyme cleavable sequences that can be used are those encoding sites recognized by microbial proteases, viral proteases, the complement cascade enzymes and enzymes of the blood coagulation/clot dissolution pathway. Other enzyme cleavable sequences will also be recognized by those skilled in the art and are intended to be included in this embodiment of the invention. Alternatively, the sequence may be selected so as to contain a site cleavable by chemical means, such as cyanogen bromide which attacks methionine residues in a peptide sequence. Another chemical means of cleavage includes the use of formic acid which cleaves at proline residues in a peptide sequence. The invention is not to be limited to the specific examples of chemical cleavage provided here but includes the use of any chemical cleavage method known to those with skill in the art.

The binding domain of a TSAR may be of any size that can be produced by the host cell. Moreover, the binding reaction of the binding domain may be the result of cooperativity between individual TSAR molecules as well as the result of the independent affinity for the ligand by a single TSAR molecule.

Once the binding domain of a TSAR has been identified, new TSARs can be created by isolating and fusing the binding domain of one TSAR to a different effector domain. The biologically or chemically active effector domain of the TSAR can thus be varied. Alternatively, the binding characteristics of an individual TSAR can be modified by varying the TSAR binding domain sequence to produce a related family of TSARs with differing properties for a specific ligand.

The biologically or chemically active effector domain can impart an enzymatic activity that can be used to identify or detect the TSAR. Alternatively it can impart a therapeutic activity, e.g. a therapeutic group with a proteolytic activity is attached to a binding domain with affinity for fibrin to result in a TSAR that binds to fibrin components in blood clots and dissolves them.

Alternatively, the effector domain can be a protein moiety that binds a metal, including but not limited to radioactive, magnetic, paramagnetic, etc. metals, and allows detection of the TSAR. Other examples of biologically or chemically active effector peptides that can be used in TSARs include but are not limited to toxins or fragments thereof, peptides that have a detectable enzymatic activity, peptides that bind metals, peptides that bind specific cellular or extracellular components, peptides that enhance expression of the TSAR molecule, peptides that interact with fluorescent molecules, and peptides that provide a convenient means for identifying the TSAR.

In the particular embodiments found in the examples infra, the full sequence of the enzyme β-galactosidase was used as the effector domain of the TSAR. This protein provides a visual means of detection upon addition of the proper substrate, e.g. X-gal or ONPG. However, the effector domain of the TSAR need not be the complete coding sequence of a protein. A fraction of a protein that is readily expressed by the host cell and that has the desired activity or function may be used.

5.2. Method to Prepare TSARs

The invention includes the process for making novel TSARs. In its most general embodiment, the process comprises the steps of: (a) inserting (i) a first nucleotide sequence encoding a putative binding domain having specificity for a ligand of choice and (ii) a second nucleotide sequence encoding a biologically or chemically active polypeptide or protein moiety into a vector downstream from 5'ATG start codon to produce a library of vectors coding for in-frame fusion proteins; (b) transforming cells with the vectors formed in step (a) to express the fusion proteins; and (c) screening the expressed fusion proteins to identify a TSAR having binding specificity for the ligand of choice, in which the first nucleotide sequence is obtained by a process of mutagenesis.

Mutagenesis, as used in this application, is intended to encompass any process which leads to the production of an alteration, including a deletion, an addition and a substitution of a nucleotide(s) in a sequence of nucleotides encoding a protein, polypeptide or peptide moiety. Hence, mutagenesis can be accomplished by chemical synthesis of an altered nucleotide sequence; by alteration induced in vitro or in vivo by any known mutagen such as ionizing radiation or a chemical mutagenic agent; and by insertion of an altered sequence generated using recombinant DNA techniques such as insertion of isolated genomic DNA, cDNA or a chemically synthesized oligonucleotide sequence. Thus, mutagenesis encompasses random, site directed or site selective techniques known to those of skill in the art. The process permits the production of a large diverse class of TSAR proteins each bearing a unique ligand-specific binding sequence fused to a biologically or chemically active effector peptide region.

According to one embodiment of the invention, step (a) of the method further comprises inserting a third nucleotide sequence encoding a linker peptide domain between the first and second nucleotide sequences. The linker domain can be either stable or susceptible to cleavage by enzymatic or chemical reagents. When the linker domain is cleavable, the heterofunctional TSAR can be used as an intermediate to prepare a unifunctional binding polypeptide or protein having specificity for a ligand of choice.

In an alternative embodiment of the invention the first nucleotide sequence comprises a member of a group of nucleotide sequences obtained by mutagenesis of the nucleotide sequence encoding the binding domain of a receptor or anti-ligand for a ligand of choice. In this embodiment, a receptor is selected from the group of naturally occurring receptors such as the variable region of an antibody, an enzyme/substrate recognition or activity site, a regulatory DNA binding protein, an RNA binding protein, a metal binding protein, an integrin or other adhesive protein, a calcium binding protein, a lectin, etc. The nucleotide sequence encoding the binding domain of the receptor is mutagenized, using techniques known to those of skill in the art, and the resulting group of nucleotide sequences are inserted as the first nucleotide sequence in step (a) of the method of the invention.

According to an alternative method of the invention using random mutagenesis, the first nucleotide sequence comprises a group of nucleotide sequences generated by random chemical synthesis or assembly of DNA fragments selected by size but not sequence. In this embodiment randomly generated nucleotide sequences are employed as a first nucleotide sequence in step (a) of the method of the invention to form a library of vectors expressing fusion proteins. The fusion proteins are screened using the ligand of choice to identify a TSAR having binding specificity for the chosen ligand. Using this mode of the present invention, the TSAR formed may have rather low binding specificity for the ligand. In such case, the nucleotide sequence encoding the binding domain of the identified TSAR is determined. The determined nucleotide sequence is then mutagenized and steps (a)–(c) of the method of the invention are repeated to identify a TSAR having enhanced binding affinity for the chosen ligand. Random mutagenesis, as used in this application, is intended to encompass mutagenesis accomplished both by random chemical synthesis of a nucleotide sequence and random alteration by any mutagenic agent as well as by assembly of DNA fragments selected by size but not by sequence.

DNA that constitutes the nucleotide sequence encoding the binding domain portion of the TSAR sequence can be chemically synthesized de novo using a) totally random synthesis; b) synthesis modeled on known binding motifs including, but not limited to, those described supra in Section 2.2 where there is some homology between the synthesized DNA and a known binding sequence but the basic sequence is subject to random change based on contamination of precursor reservoirs during synthesis; or c) by minor alteration of the sequences of known binding domains based on the limited and defined change of bases within the sequence. Alternatively, binding domain DNA can be produced by insertion of nonselected sheared genomic DNA or cDNA fragments into the p340 vector. The resulting novel molecules are screened using methods known to those of skill in the art, for increased or decreased affinity, or avidity for known ligands or for new specificities for novel ligands, including new specificities detected using nonaqueous solutions.

Since each individual TSAR construct can have a different yet representative fragment of binding domain DNA, each batch of recombinants produced will represent a distinct library of relatedness. The frequency of relatedness between each member of the library can be calculated and will depend on the method used to generate the binding domain DNA. Where variation within the library is large, high density screening methods and lambda vectors can be used. For example, if oligonucleotides are synthesized on an automated DNA synthesizer like the Applied Biosystems machine, a microprocessor allows the user to program additions to growing oligonucleotide chains from any one of seven precursor reagent bottles. Addition of nucleotides coding for known bases in a sequence is done in the customary fashion using four single precursor bottles, one for each pure precursor. In the positions where nucleotides are varied, a mixture of four precursor nucleotides from a fifth bottle will be programmed. Insertion of random nucleotides at only nine amino acid codons allows up to $7.9 \times 10^{11}$ possible proteins to be encoded and subsequently expressed. Since recombinant phage libraries produced in vitro generally have no more than $10^8$–$10^{10}$ members, every library constructed will have no identical TSAR clones.

In the specific examples, (see, infra, Sections 8 and 9) the binding domain DNA was produced in a series of steps allowing assembly of complementary oligonucleotides that were first chemically synthesized, then cloned and sequenced by the dideoxynucleotide chain termination method. Individual DNA fragments encompassing the oligonucleotide were then reassembled using appropriate restriction sites on the end of each fragment and appropriate restriction sites in the recipient plasmids. DNA fragments of up to 367 nucleotides long with a coding capacity of over one hundred and twenty amino acids have been produced. Because known binding sites, especially those described in Section 2 supra fall within this size range, the size of the inserted fragment that can be synthesized will not limit the binding domain DNA that can be generated and thus will not limit the specificity that can be detected.

A nucleotide sequence encoding an effector domain having the desired chemical or biological activity is obtained using methods familiar to those of skill in the art. Such methods include, but are not limited to, polymerase chain reaction (PCR) amplification of the desired DNA and determination of its nucleotide sequence. Alternatively, sequences encoding the desired activity can be detected by hybridization using an oligonucleotide (or an oligonucleotide family that includes all possible codon translations of the peptide with desired activity) having a sequence that encodes a known portion of the desired active effector protein. The oligonucleotide(s) hybridization allows the purification of restriction fragments of genomic DNA encoding the active protein. The genomic DNA or cDNA copy is then sequenced. The nucleotide sequence can be synthesized or an appropriate restriction fragment can be isolated and juxtaposed to the binding domain sequence in a vector through use of a linker adaptor or other means to produce an in-frame fusion protein. Alternatively, if the nucleotide sequence of the protein of desired activity is known and has been cloned already, isolation of the nucleotide sequence encoding the desired activity can be more readily accomplished by simple purification of the restriction fragment containing the appropriate sequence.

The skilled artisan will recognize that to achieve transcription and translation of the TSAR gene, in the method of expressing the TSAR protein of the present invention, the gene must be placed under the control of a promoter compatible with the chosen host cell. A promoter is a region of DNA at which RNA polymerase attaches and initiates transcription. The promoter selected may be any one that has been synthesized or isolated that is functional in the host. For example, E.coli, a commonly used host system, has numerous promoters such as the lac or trp promoter or the promoters of its bacteriophages or its plasmids. Also synthetic or recombinantly produced promoters such as the $P_{TAC}$ promoter may be used to direct high level production of the segments of DNA adjacent to it.

Signals are also necessary in order to attain efficient translation of the TSAR gene. For example in E.coli mRNA, a ribosome binding site includes the translational start codon AUG or GUG in addition to other sequences complementary to the bases of the 3' end of 16S ribosomal RNA. Several of these latter sequences such as the Shine/Dalgarno sequence have been identified in E.coli and other suitable host cell types. Any S/D-ATG sequence which is compatible with the host cell system can be employed. These S/D-ATG sequences include, but are not limited to, the S/D-ATG sequences of the cro gene or N gene of coliphage lambda, the tryptophan E, D, C, B or A genes, a synthetic S/D sequence or other S/D-ATG sequences known and used in the art. Thus, regulatory elements control the expression of the polypeptide or proteins to allow directed synthesis of the reagents in cells and to prevent constitutive synthesis of products which might be toxic to host cells and thereby interfere with cell growth.

A number of methods exist for the insertion of DNA fragments into cloning vectors in vitro. DNA ligase is an enzyme which seals nicks between adjacent nucleotides in a duplex DNA chain; this enzyme may therefore be used to covalently join the annealed cohesive ends produced by certain restruction enzymes or to join blunt ended fragments together. In addition, the enzyme terminal deoxynucleotidyl transferase may be employed to form homopolymeric 3'-single-stranded tails at the ends of fragments. For example, by the addition of oligo(dA) sequences to the 3' end of one population, and oligo (dT) blocks to the 3' ends of a second population, the two types of molecules can anneal to form dimeric circles. Any of these methods may be used to fuse the different domains of the TSAR protein into specific sites in the vector.

Thus the sequences coding for the different regions of the TSAR protein are fused in a chosen vector in a specific relationship to promoter and control elements so that the TSAR sequence is in the correct reading frame with respect to the ATG sequence that specifies the start of the TSAR protein. Vectors encoding TSARs can be viruses, bacterial plasmids, phage, eukaryotic cell viruses or eukaryotic plasmids, or any other vector known to those with skill in ,the art that allows a TSAR to be easily produced and manipulated in different host cells. The vector employed will typically have a marker function, such as ampicillin resistance or tetracycline resistance, so that cells transformed with TSAR vectors can be identified. The vector employed may be any of the known expression vectors or their derivatives; among the most frequently used are plasmid vectors such as pBR322, pAC1005, pSC101, pBR325, or derivatives of these vectors; bacteriophage vectors such as lambda or its recombinant derivatives like lamda-gt11, M13 or its derivatives like M13mp7, T7 or T4; SV40, EBV, vaccinia and adenovirus vectors; and yeast or insect vectors. A specifically exemplified vector that is usefully employed is p340 (see section 7.4 infra). The vector is selected for its compatibility with the chosen host cell system. Although bacteria, particularly E. coli, have proven very useful for the high yield production of a soluble TSAR protein, and therefore is the preferred host, the invention is not so limited. The present method contemplates the use of any culturable unicellular organism as host; for example, eukaryotic hosts such as yeast, insect, plant and mammalian cells are also potential hosts for TSAR production. The selection of an appropriate expression system, based on the choice of a host cell, is well within the ability of the skilled artisan.

TSAR phage clones can be grown to a high density and representative products can be transferred as a mirror image onto nitrocellulose filters or analogous solid supports after expression of the TSAR genes. Screening large numbers of plaques containing TSAR proteins can be accomplished using techniques that are similar to those using radioactive nucleic acid probes, where the ligand replaces the radioactive nucleic acid probe. In one embodiment the ligand can be bound to the support. TSARs with affinity for the ligand will be identified by their selective association to the filter because of ligand binding. Alternatively, the TSARs can be immobilized and the properties of the ligand can be used to identify clones that bind the ligand. Direct and indirect methods that identify the ligand, the TSAR protein or other components that bind to either one can be used to screen recombinant libraries and are well known in the art. See for example, Young and Davis in DNA Cloning: A Practical Approach Vol 1 (ed. D. M. Glover) IRL Press, Oxford pp. 49–78; Young and Davis, Proc. Nat'l. Acad. Sci. 80: 1194 (1983); Kemp and Cowman, Proc. Nat'l Acad. Sci. 78: 4520 (1981); Unit 6.7, "Screening with Antibodies", Current Protocols in Molecular Biology, John Wiley and Sons, New York, pp. 6.7.1–6.7.5 (1987).

Binding to individual ligands can then be assayed for each filter using repetitive rounds with a new interaction tested each round. Individual phage plaques that are positive in the binding assay can be isolated from others in the library. Rapid purification of the specific TSAR protein can be achieved by virtue of the association of the effector portion of the chimeric TSAR molecule for its substrate, eg. purification of β-galactosidase containing TSARs by affinity of the β-galactosidase for p-aminophenyl-1-thio-β-D-galactopyranoside-Sepharose.

5.3. Applications and Uses of TSARs

TSARs prepared according to the novel methods of the invention are useful for in vitro and in vivo applications which heretofore have been performed by binding regions of antibodies, DNA binding proteins, RNA binding proteins, metal binding proteins, nucleotide fold and GTP binding proteins, calcium binding proteins, adhesive proteins such as integrins, adhesins, lectins, enzymes, or any other small peptide or portion of a macromolecule that has binding affinity for a ligand.

The TSAR products can be used in any industrial or pharmaceutical application that requires a peptide binding moiety specific for any given ligand. The TSARs can also be intermediates in the production of unifunctional binding peptides that are produced and selected by the method of the invention to have a binding affinity, specificity and avidity for a given ligand. Thus, according to the present invention, TSARs are used in a wide variety of applications, including but not limited to, uses in the field of biomedicine; biologic control and pest regulation; agriculture; cosmetics; environmental control and waste management; chemistry; catalysis; nutrition and food industries; military uses; climate control; pharmaceuticals; etc. The applications described below are intended as illustrative examples of the uses of TSARs and are in no way intended as a limitation thereon. Other applications will be readily apparent to those of skill in the art and are intended to be encompassed by the present invention.

The TSARs are useful in a wide variety of in vivo applications in the fields of biomedicine, bioregulation, and control. In these applications, the TSARs are employed as mimetic replacements for compositions such as enzymes, hormone receptors, immunoglobulins, metal binding proteins, calcium binding proteins, nucleic acid binding proteins, nucleotide binding proteins, adhesive proteins such as integrins, adhesins, lectins, etc.

Other in vivo uses include administration of TSARs as immunogens for vaccines, useful for active immunization procedures. TSARs can also be used to develop immunogens for vaccines by generating a first series of TSARs specific for a given cellular or viral macromolecular ligand and then developing a second series of TSARs that bind to the first TSARs i.e. the first TSAR is used as a ligand to identify the second series of TSARs. The second series of TSARs will mimic the initial cellular or viral macromolecular ligand site but will contain only relevant peptide binding sequences, eliminating irrelevant peptide sequences. Either the entire TSAR developed in the second series or the binding domain thereof can be used as an immunogen for an active vaccination program.

In in vivo applications TSARs can be administered to animals and/or humans by a number of routes including injection (e.g. intravenous, intaperitoneal, intramuscular, subcutaneous, intraauricular, intramammary, intraurethrally, etc.), topical application, or by absorption through epithelial or mucocutaneous linings. Delivery to plants, insects and protists for bioregulation and/or control can be achieved by direct application to the organism, dispersion in the habitat, addition to the surrounding environment or surrounding water, etc.

In the chemical industry, TSARs can be employed for use in separations, purifications, preparative methods, and catalysis.

In the field of diagnostics, TSARs can be used to detect ligands occurring in lymph, blood, urine, feces, saliva, sweat, tears, mucus, or any other physiological liquid or solid. In the area of histology and pathology, TSARs can be used to detect ligands in tissue sections, organ sections, smears, or in other specimens examined macroscopically or microscopically. TSARs can also be used in other diagnostics as replacements for antibodies, as for example in hormone detection kits, or in pathogenic detection kits etc. where a pathogen can be any pathogen including bacteria, viruses, mycoplasma, fungi, protozoans, etc. TSARs may also be used to define the epitopes that monoclonal antibodies bind to by using monoclonal antibodies as ligands for TSAR binding, thereby providing a method to define the conformation of the original immunogen used to develop the monoclonal antibody.

The following examples are provided to illustrate this invention. However, they are not to be construed as limiting the scope of the invention, which scope is determined by this entire specification including the appended claims.

6. EXAMPLE: MATERIALS AND METHODS

6.1. Conditions for Restriction Enzyme Digestion

Enzymes were obtained from commercial sources (New England Biolabs) and digestions were carried out as recommended by the manufacturer.

6.2. Bacterial Strains and Plasmids

E. coli JM101 (SupE, thi, Δ(lac-pro) [F', traD36, proAB, lac$^q$Z ΔM15] (P-L Pharmacia, Milwaukee, Wis.) was transformed as described in Hanahan, J. Mol. Biol. 166:557 (1983). Plasmid pKK233-2 was obtained from P-L Pharmacia; plasmid pBS$^+$ was from Stratagene. Several plasmids were constructed as modifications of pBS$^+$ cloning vector (Stratagene) to allow for DNA amplification and ease in sequencing each oligomer. Plasmid p282 was produced by insertion of a 28 base oligonucleotide adapter (5'AGCTTCCATGGTCGCGACTCGAGCTGCA-3') between the HinD III and Pst I sites of the pBS$^+$ multiple cloning region. As a result, the modified plasmid p282 no longer contains its original Sph I restriction site but encodes additional sites for Nco I, Nru I and Xho I. The vector p287 was constructed by adding the sequence GCTCGACTCGC-GACCATGGA between the PstI and Hind III restriction sites of pBS$^+$, thereby deleting an SphI site of pBS$^+$ and adding NcoI, NruI and XhoI restriction sites. Another transitional plasmid, plasmid p350, was used to clone other binding domain DNA fragments. Plasmid p350 was produced by annealing oligonucleotide 737 [5'-AGCTGATTAAATAAGGAGGAATAACCATGGCTGCA] and oligonucleotide 738 [5'-GCCATGGTTATTCCTCCTTATTTAATC] which were then inserted into Hind III and Pst I digested plasmid pBS$^+$. Other plasmid constructs are as described in this application.

Plasmid DNA was prepared by the alkaline lysis method [Birnboim and Doly, Nucl. Acids Res. 7: 1513 (1979)].

6.3. Oligonucleotide Assembly

Oligonucleotides were synthesized from CED phosphoramidites and tetrazole obtained from American Bionetics. Oligonucleotides were kinased with T4 polynucleotide kinase according to manufacturer's suggestions (New England Biolabs). The kinase was inactivated by heating at 65° C. Oligonucleotide mixtures were annealed by heating at 65–85° C. for 15 minutes and cooled slowly to room temperature. The annealed oligonucleotides were ligated with 10 U T4 ligase, ligated products were separated on a 6% polyacrylamide gel, and the fragments were recovered by electroelution.

6.4. DNA Sequencing

The DNA sequences of inserted fragments and oligonucleotides were determined by the chain termination method of Sanger et al., Proc. Natl. Acad. Sci. 74:5463 (1977), incorporating the modifications of Biggen et al., Proc. Natl. Acad. Sci. 80:3963 (1983), Hattori and Sakakai, Anal. Biochem. 152:232 (1986), and Bankier et al., Methods Enzymol. 155: 51–93 (1987).

7. EXAMPLE: CONSTRUCTION OF AN EXPRESSION VECTOR

7.1. The Initial Vector pJG200

Plasmid pJG200 was the starting material that was modified to produce a general TSAR expression vector. The initial plasmid, pJG200, contained target cistrons that were fused in the correct reading frame to a marker peptide with a detectable activity via a piece of DNA that codes for a protease sensitive linker peptide [Germino and Bastia, Proc. Natl. Acad. Sci. USA 81:4692 (1984); Germino et al., Proc. Natl. Acad. Sci. USA 80:6848 (1983)]. The promoter in the original vector pJG200 was the PR promoter of phage lambda. Adjacent to the promoter is the gene for the $C_I$857 thermolabile repressor, followed by the ribosome-binding site and the AUG initiator triplet of the cro gene of phage lambda. Germino and Bastia inserted a fragment containing the triple helical region of the chicken pro-2 collagen gene into the Bam HI restriction site next to the ATG initiator, to produce a vector in which the collagen sequence was fused to the lacZ β-galactosidase gene sequence in the correct translational phase. A single Bam HI restriction site was regenerated and used to insert the plasmid R6K replication initiator protein coding sequence.

The plasmid pJG200 expressed the R6K replicator initiator protein as a hybrid fusion product following a temperature shift which inactivated the $C_I$857 repressor and allowed transcription initiation from the PR promoter. Both the parent vector construct with the ATG initiator adjacent to and in frame with the collagen/β-galactosidase fusion (noninsert vector), and pJG200 containing the R6K replicator initiator protein joined in frame to the ATG initiator codon (5') and the collagen/β-galactosidase fusion (3') (insert vector), produced β-galactosidase activity in bacterial cells transformed with the plasmids. As a result, bacterial strains containing plasmids with inserts are not distinguishable from strains containing the parent vector with no insert.

7.2. Removal of the $P_R C_I$857 Repressor and Amino Terminus of Cro

The first alteration to pJG200 according to this invention was the removal and replacement of the Eco RI-Bam HI fragment that contained the $P_R$ promoter, $C_I857$ repressor and amino terminus of the cro protein which provided the ATG start site for the fusion proteins. An oligonucleotide linker was inserted to produce the p258 plasmid, which maintained the Eco RI site and also encoded the additional DNA sequences recognized by Nco I, Bgl II and Bam HI restriction endonucleases. This modification provided a new ATG start codon that was out of frame with the collagen/β galactosidase fusion. As a result, there is no β-galactosidase activity in cells transformed with the p258 plasmid. In addition this modification removed the cro protein amino terminus so that any resultant recombinant fusion products inserted adjacent to the ATG start codon will not have cro encoded amino acids at their amino terminus. In contrast, recombinant proteins expressed from the original pJG200 vector all have cro encoded amino acids at their amino terminus.

7.3. Addition of the $P_{TAC}$ Promoter, Shine Dalgarno Sequence and ATG Condon In the second step of construction of a TSAR expression vector, a restriction fragment, the Eco RI-Nco I fragment of pKK233-2 (Pharmacia Biochemicals, Milwaukee, Wis.), was inserted into the Eco RI-Nco I restriction sites of plasmid p258 to produce plasmid p277. As a result, the p277 plasmid contained the $P_{TAC}$ (also known as $P_{TRC}$) promoter of pKK233-2, the lacZ ribosome binding site and an ATG initiation codon.

In the p277 plasmid, the insertion of a target protein sequence allows its transcription from an IPTG inducible promoter in an appropriate strain background. The appropriate strain background provides sufficient lac repressor protein to inhibit transcription from the uninduced $P_{TAC}$ promoter. Appropriate strains that can be used include JM101 or XL1-Blue. Because cells can be induced by the simple addition of small amounts of the chemical IPTG, the p277 plasmid provides a significant commercial advantage over promoters that require temperature shifts for induction. For example, induction by the $P_R$ promoter requires a temperature shift to inactivate the $C_I857$ repressor inhibiting pJG200's PR promoter. Induction of commercial quantities of cell cultures containing temperature inducible promoters require the inconvenient step of heating large volumes of cells and medium to produce the temperature shift necessary for induction.

One additional benefit of the promoter change is that cells are not subjected to high temperatures or temperature shifts. High temperatures and temperature shifts result in a heat shock response and the induction of heat shock response proteases capable of degrading recombinant proteins as well as host proteins [See Grossman et al., Cell 38:383 (1984); Baker et al., Proc. Natl. Acad. Sci. 81: 6779 (1984)].

7.4. Improvement of the Ribosome Binding Site

The p277 expression vector was further modified by insertion of twenty-nine base pairs, namely 5'CATGTATC-GATTAAATAAGGAGGAATAAC3' into the Nco I site of p277 to produce plasmid p340-1. This 29 bp sequence is related to, but different from, one portion of the Schoner "minicistron" sequence [Schoner et al., Proc. Nat'l. Acad. Sci. 83: 8506, (1986)]. The inclusion of these 29 base pairs provides an optimum Shine/Dalgarno site for ribosomal/mRNA interaction. The p340-1 expression vector significantly differs from pJG200 because it contains a highly inducible promoter suitable for the high yields needed for commercial preparations, an improved synthetic ribosome binding site region to improve translation, and a means to provide a visual indicator of fragment insertion upon isolation. The steps in the construction of vector p340-1 are diagrammed in FIG. 1.

8. EXAMPLE: CONTROL FUSION PROTEIN AND CONSTRUCTION OF TSAR-1

A plasmid construct was made that included a portion of the DNA sequence encoding the variable domain of a murine monoclonal antibody specific for a dansyl hapten, fused to a DNA sequence encoding a collagenase sensitive site and β-galactosidase.

Assembly of the synthetic oligomers was carried out in multiple steps. In general, single stranded oligonucleotides bearing complementary overhangs were annealed and ligated to produce three separate double-stranded fragments whose specific construction is described below. Subsets of these double stranded oligonucleotides were assembled in separate annealing and ligation reactions to produce sub-fragments. Before assembly, synthetic oligomers were kinased with 10 units of T4 polynucleotide kinase. To prevent concatenation during ligation, the 5' terminal oligomers on either strand were not phosphorylated. A modified pBS$^+$ vector (Stratagene) was produced to simplify subsequent cloning steps (see Section 6.2, sura). The modified vector, designated p287, was made by changing the pBS$^+$ vector HindIII restriction site to a NcoI site. The synthetic oligomers were separately cloned into vector p287 to allow DNA amplification and sequence verification by dideoxy-nucleotide sequencing. Insertion of the assembled fragments into the modified vector produced different recombinant plasmids each containing a portion of a potential binding domain DNA region proceeding from amino to carboxy terminus respectively as described below. Following ligation, each plasmid DNA was transformed separately into competent E. coli JM101.

The first fragment was composed of six oligonucleotides and included the sequence from the XhoI site to the HindIII site of the sequence shown in FIG. 2. This fragment (B) was inserted into the XhoI and HindIII site of p287 to yield p306.

A second fragment was composed of four oligonucleotides incorporating the sequence between HindIII and BamH I of the sequence shown in FIG. 2. This fragment (C) was cloned into HindIII and BamH I digested p287 to produce p320. The XhoI/HindIII fragment (B) from p306 and the HindIII/BamH I fragment (C) from p320 were subcloned into p287 that had been digested with XhoI and BamH I to yield p321 in which fragments B and C were juxtaposed at the HindIII site.

A third fragment containing the sequence including the AATTC nucleotides of the EcoR I site to the XhoI site of FIG. 2 was produced from six oligonucleotides. This fragment (A) was cloned into EcoR I and XhoI digested p287 to yield plasmid p322.

The XhoI/BamH I B/C fragment of p321 and the NcoI/XhoI subfragment of p322, the latter containing the A fragment sequence, were subcloned into NcoI and BamH I digested p277 (see Section 7.3) to yield p323.

Figure 3:
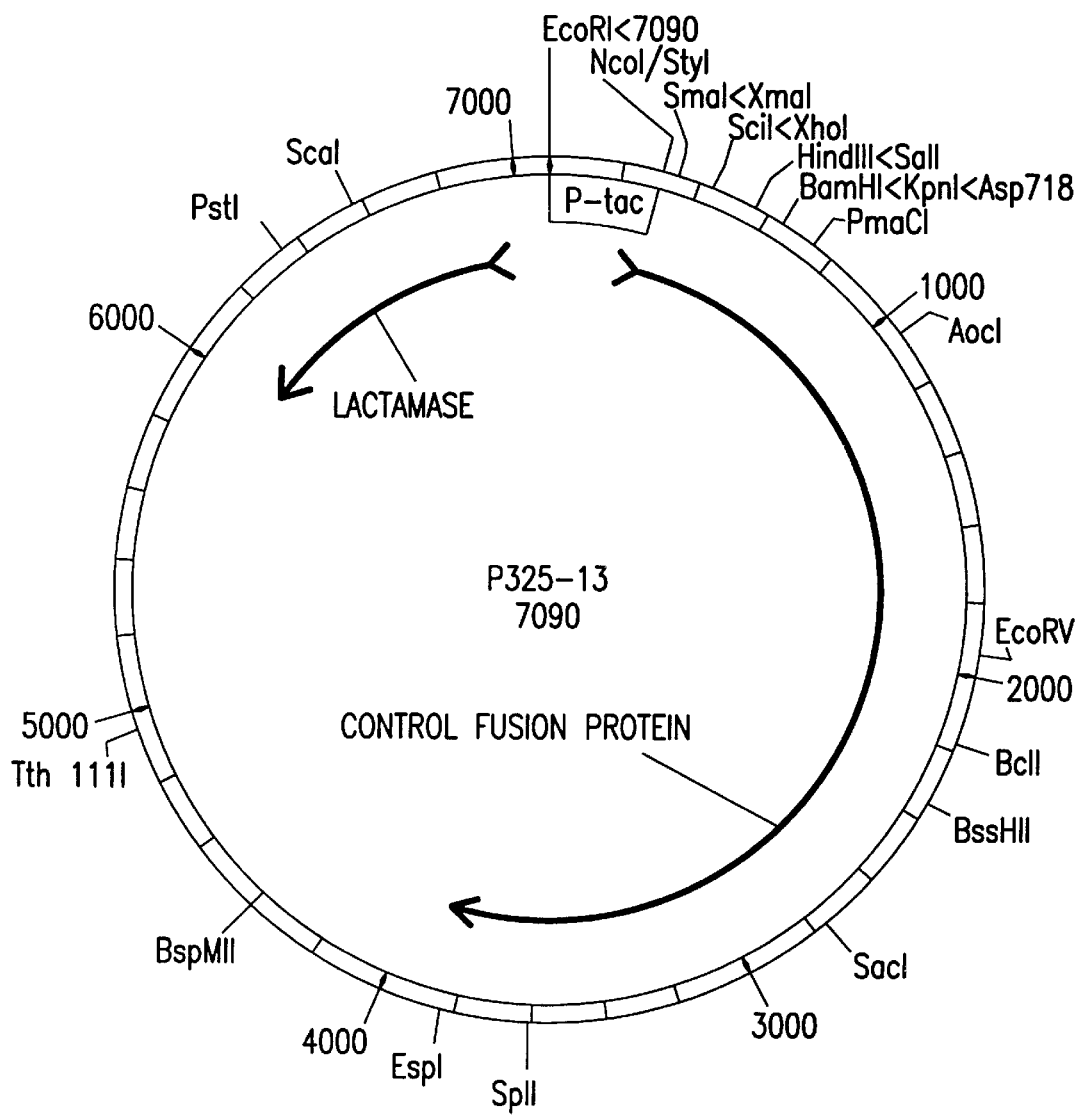
FIG. 3 is a diagram of the plasmid p325-13 which encodes the control fusion protein.
Figure 5:
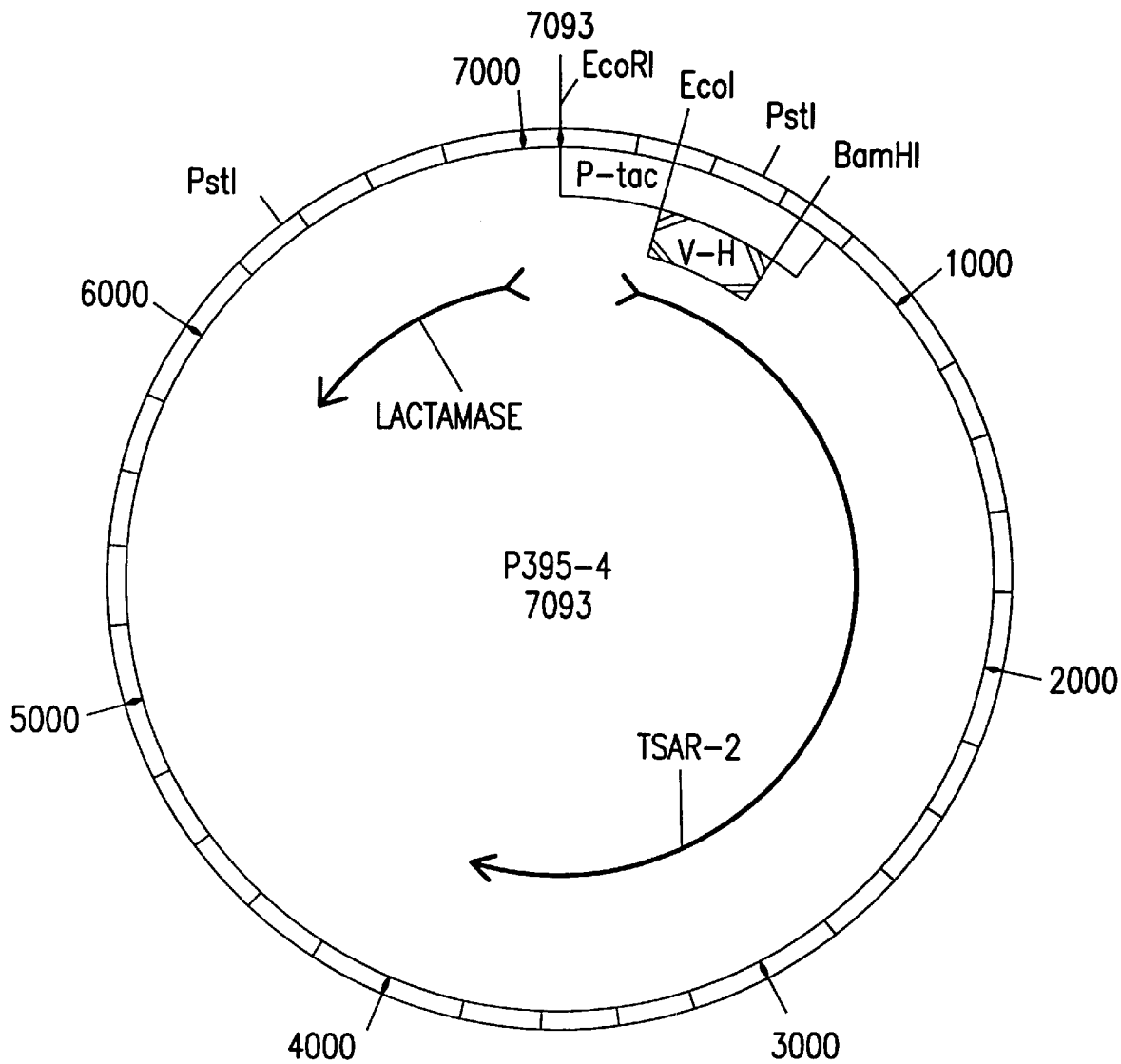
FIG. 5 is a diagram of the plasmid p395-4 which encodes TSAR-2.

The mini-cistron fragment was inserted into the NcoI site of the modified p277 i.e., p323, to yield the construct p325-13. A diagram of p325-13 is shown in FIG. 3.

Although the DNA sequence encoding the fusion protein expressed by p325-13 contained a portion of the sequence of the variable domain of an antibody specific for a dansyl hapten, binding studies indicated that the fusion protein had no specific binding affinity for the dansyl moiety. The fusion protein expressed by p325-13 was, however, cleavable by collagenase and could be detected in vitro by the β-galactosidase activity of its carboxyl terminal end. As illustrated in FIG. 7, the fusion protein expressed by p325-13 also had no detectable specific binding affinity for lysozyme although the amino-terminal end of the fusion protein shares significant homology with the variable region of the monoclonal antibody having affinity for hen egg lysozyme reported by Darsley and Reed, EMBO J. 4: 393 (1988).

The expressed fusion protein (hereinafter termed "control fusion protein") could be modified to produce a TSAR-1 according to the present invention as follows. Random mutagenesis of the oligonucleotide sequence encoding the amino-terminal end of the control fusion protein, followed by expression and screening the family of related fusion proteins formed using a dansyl or lysozyme ligand would result in a TSAR having the desired binding domain with affinity for the dansyl or lysozyme ligand, a collagenase sensitive linker domain and an effector domain having β-galactosidase activity. For example, chemical synthesis of the oligonucleotides encoding the amino-terminal end of p325-13 using programmed reservoir contamination results in a family of oligonucleotides which, when expressed, yields a family of fusion proteins related to the control fusion protein. Screening this family of related fusion proteins results in a TSAR termed "TSAR-1" having a binding domain with affinity for dansyl or lysozyme and an effector domain having β-galactosidase activity.

Screens are accomplished by replicating cells containing vectors expressing the family of fusion proteins, immobilizing expressed proteins from vector containing cells to filter, applying either the lysozyme or the dansyl ligand to the filters, washing the unbound ligand from the filters, detecting the bound ligand, and then examining the filters for ligand binding to identify vectors expressing a dansyl or lysozyme binding moiety.

9. EXAMPLE: TSAR-2 CONSTRUCTION

A plasmid construct was made that includes a binding domain consisting of a chemically synthesized modified sequence designed from the variable domain of a monoclonal antibody with affinity for the G-Loop-2 region of hen egg lysozyme, as reported by Darsley and Reed, EMBO J. 4: 393 (1988). The modified DNA sequence was fused to DNA sequences encoding a collagenase sensitive site and β-galactosidase. Assembly of the synthetic oligomers was carried out in multiple steps.

In general, single-stranded oligonucleotides bearing complementary overhangs were annealed and ligated to produce double-stranded subfragments encoding the TSAR-2 binding domain. These double-stranded oligonucleotides were then assembled to produce two separate double-stranded fragments that together encode the TSAR-2 binding domain. The specific construction of these two fragments is described below. Before assembly, synthetic oligomers were kinased with 10 units of $T_4$ polynucleotide kinase. To prevent concatenation during ligation, the 5' terminal oligomer on either strand was not phosphorylated. Following ligation, each plasmid DNA was transformed separately into competent *E. coli* JM101.

The synthetic oligomers constituting the two double-stranded fragments encoding the TSAR-2 binding domain were separately cloned into the modified pBS$^+$ vectors p287 or p350 (described in Section 5 supra) to allow DNA amplification and sequence verification by dideoxynucleotide sequencing. The first fragment was composed of six oligonucleotides and included the sequence from the NcoI site to the XbaI site of the sequence shown in FIG. 4. This fragment was cloned into NcoI and XbaI digested p350 to produce plasmid p374-2.

The second fragment was composed of ten oligonucleotides and included the sequence from the XbaI site to the BamH I site of the sequence shown in FIG. 4. This fragment was cloned into XbaI and BamH I digested plasmid p287 to produce plasmid p382-9.

The first NcoI/Xba I fragment of p374-2 and the second XbaI/BamH I fragment of p382-9 were then subcloned into NcoI and BamH I digested plasmid p340 (see Section 7, supra) to produce plasmid p395-4, the TSAR-2 expression vector. A diagram of plasmid p395-4 is shown in FIG. 5.

The resulting protein fusion product, TSAR-2, shares significant sequence homology in the binding domain with the control fusion product described in Section 9 and is identical to the control fusion protein in all other parts of the molecules. A comparison of the sequence similarity of the control fusion product and TSAR-2 is provided in FIG. 6. TSAR-2 differs in binding activity when compared to the control as demonstrated in FIGS. 7 and 9.

10. EXAMPLE: CELL GROWTH AND EXPRESSION FOR TSAR PURIFICATION

*E. coli* cells harboring the TSAR vectors or the control fusion protein were grown in 10 liters of 2× YT fermentation medium. [Miller, Experiments in Molecular Genetics, Cold Spring Harbor Laboratory, Cold Spring Harbor N.Y. p. 433 (1974)]. Cells were grown in a MagnaFerm Bench Top Fermentor Model MA-100 (New Brunswick Scientific G.) from a dilution of an overnight culture grown in M9 medium to an $OD_{590}$ of about 0.5. [Miller, supra, p.431] supplemented with ampicillin. Cells were cultured in the YT fermentation medium to an $OD_{590}$ of 8 at which time IPTG was added to 1 mM and lactose was added to 5 mM. During fermentation the pH was maintained at 7. β-galactosidase activity was monitored by a colorimetric assay with ONPG as substrate using the protocol of Miller, supra, p. 433. When β-galactosidase activity plateaued, the cells were harvested by centrifugation and stored at −20° C.

11. EXAMPLE: PURIFICATION OF THE CONTROL FUSION PROTEIN AND TSAR-2

*E. coli* cells containing either the p325-13 expressing the control fusion protein or the p395-4 plasmid expressing TSAR-2 were harvested by centrifugation and stored frozen. Frozen cell paste was resuspended in 0.05M Tris-HCl pH 8, 0.05M EDTA, 15% sucrose with freshly dissolved lysozyme at 1 mg/ml in a volume of buffer such that 1 g of cell paste was resuspended in 5 ml of buffer. The cells were incubated on ice for 30 min. and then frozen at −70° C., thawed rapidly and sonicated briefly to shear DNA. PMSF was added to 1mM and the suspension was centrifuged at 27,000×g for 30 min. at 4° C. Nucleic acids were precipitated by dropwise addition of 10% streptomycin sulfate.

The supernatant was adjusted to 1.6 M NaCl and applied to a p-aminophenyl-1-thio-β-D-galactopyranoside-Sepharose column using the procedure of Ullmann [Gene 29: 27 (1984)]. A 3×7 cm column was routinely used for 24 g of frozen cell paste. The TSAR/control protein was eluted with 0.1 M sodium borate, pH 5 and promptly precipitated with 40% ammonium sulfate. The fractions were assayed for β-galactosidase activity and the active fractions were pooled. Protein was collected by centrifugation at 12,000×g for 20 min. at 4° C. The TSAR/control protein precipitate was dissolved in and dialyzed overnight against 0.05 M Tris-HCl, pH 8.3, 0.15 M NaCl, 0.02% sodium azide, 0.1% polyethylene glycol 8000 at 4° C. The purity of the TSAR/control protein was monitored as units of β-galactosidase per mg of protein, as measured by the Bradford Assay (Bio-Rad). TSAR/control protein was quantitated by colorimetric assay for β-galactosidase activity using ONPG as substrate.

12. EXAMPLE: LYSOZYME BINDING ASSAY OF TSAR-2

The binding affinities and specificities of the control fusion protein and TSAR-2 to Chicken Egg Lysozyme HCl (Sigma Chemical Co., St. Louis, Mo.) were compared as follows:

a) Two 96-well SeroCluster EIA plates (elisa immunoassay plates, Costar, Cambridge, Mass.) were coated overnight; one with 25 μg/ml chicken egg lysozyme in 1× TBS (10 mM Tris-HCl, pH 8.0, 15 mM NaCl in distilled $H_2O$), the second with 25 μg/ml bovine serum albumin (BSA) also in 1× TBS. The volume placed in each well was 100 μl.

b) Fourteen hours later the coating material was removed by aspiration. Subsequently, 25 μg/ml BSA in 1× TBST (TBS with Tween-20 added to a final concentration of 0.05%) was added at 200 μl/well and plates were incubated for 2 hours at room temperature to block additional binding.

c) After the 2 hour blocking period, both plates were washed 8 times with 1× TBST.

d) Dilutions of the control and TSAR-2 proteins were prepared during the 2 hour blocking reaction. To determine what dilutions were required, the control and TSAR-2 proteins were first assayed for beta-galactosidase activity, and the activities compared. Because TSAR-2 had only a very slightly higher beta-galactosidase activity than the control on an activity to mass basis (the ratio being 1:1.05), equal concentrations of each were used in the assay.

Purified control and TSAR-2 proteins were diluted to 100, 75, 50, 25, 10, 5, 1, and 0.1 μg/ml. The dilutions techniques. 1× TBST was employed as the dilutant. The plates were loaded with 100 μl/well as follows:

|   | CONTROL | | | | | TSAR-2 | | | | | BLANK | |
| --- | --- | --- | --- | --- | --- | --- | --- | --- | --- | --- | --- | --- |
|   | 1 | 2 | 3 | 4 | 5 | 6 | 7 | 8 | 9 | 10 | 11 | 12 |
|   | 100 μg/ml | | | | | 100 μg/ml | | | | | 1X TBST | |
| B | 75 μg/ml | | | | | 75 μg/ml | | | | | | |
| C | 50 μg/ml | | | | | 50 μg/ml | | | | | | |
| D | 25 μg/ml | | | | | 25 μg/ml | | | | | | |
| E | 10 μg/ml | | | | | 10 μg/ml | | | | | | |
| F | 5 μg/ml | | | | | 5 μg/ml | | | | | | |
| G | 1 μg/ml | | | | | 1 μg/ml | | | | | | |
| H | 0.1 μg/ml | | | | | 0.1 μg/ml | | | | | | |

Parallel plates 1 and 2 were run treated as in (a). One plate was coated with chicken egg lysozyme and the second was coated with BSA as an additional control ligand. The incubation time to allow binding in this assay was 2 hours at 21° C.

e) The plates were washed 8 times with 1× TBST.

f) After aspirating the final wash buffer, 50 μl of Z buffer (60 mM $Na_2HPO_4.7H_2O$; 40 mM $NaH_2PO_4.H_2O$; 10 mM KCl; 1 mM $MGSO_4.7H_2O$; 50 mM beta-mercaptoethanol) was added to each well (including the blank control wells). 50 μl/ml of ONPG (4 mg/ml in distilled $H_2O$) was then added to each well (including the blank wells).

g) Multiple determinations of optical density were done over approximately 45 minutes. The plates were read at 405 nm in a 5 and 10 minute kinetic run. The results are expressed as the change in optical density over time.

h) The color change was stopped by the addition of 50 μl/well 1M $Na_2CO_{31}$ and a final endpoint reading was taken. All analyses were done using a Molecular Devices, Inc. (Palo Alto, Calif.) $V_{max}$ (TM) kinetic microplate reader. The data was collected and analyzed using soft (TM) calorimetric analysis software and an IBM-PC compatible computer.

Figure 8A:
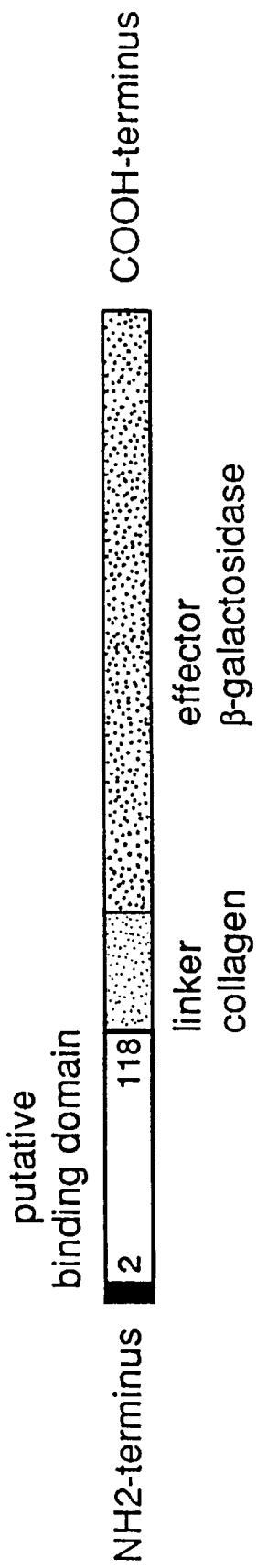
FIG. 8 is a diagram of the control fusion and TSAR-2 proteins, illustrating the "binding" domains, the linker domains and the effector domains of these heterofunctional proteins.
Figure 8B:
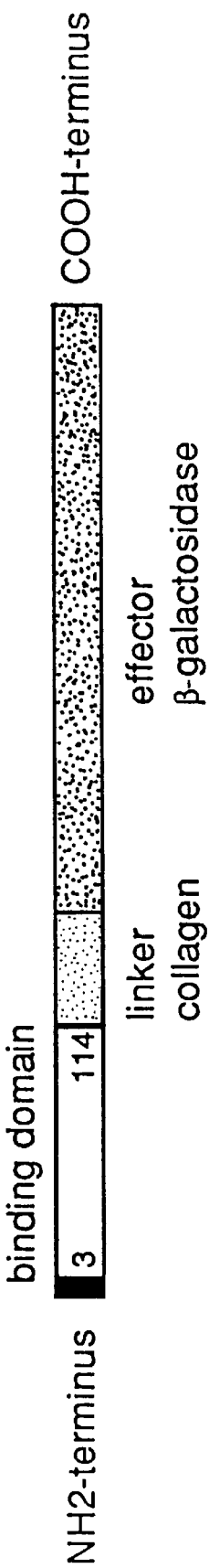

As can be seen from FIG. 9, TSAR-2 protein is able to bind to chicken egg lysozyme but not to bovine serum albumin (BSA). In addition, the control fusion protein does not bind to chicken egg lysozyme when compared to TSAR-2 even though the control fusion protein and TSAR-2 share very close sequence similarities since they are absolutely identical in all portions of the protein except the binding domain (amino acids 2–118 for the control fusion protein and 3–114 for TSAR-2 as diagrammed in FIG. 8). Although not exactly similar in the binding domain, the two proteins are closely related in binding domain sequence as is apparent from the comparison of the sequence of these regions presented in FIG. 6 and the schematic of FIG. 8.

TSAR-2 binding specificity and affinity for different lysozymes was analyzed using these same kinetic procedures by comparison of the binding of TSAR-2 to chicken egg lysozyme and human milk lysozyme. Although TSAR-2 had significant binding affinity for chicken egg lysozyme as indicated in FIG. 9, TSAR-2 had a very low affinity for human milk lysozyme that could be detected in kinetic assays only at high concentrations of protein (between 50–100 μg/ml for human milk lysozyme as compared to binding to chicken egg lysozyme that was detectable at concentrations below 1 μm/ml). Thus, TSAR-2 in this example is an illustration of a heterofunctional protein produced by the method of the invention which has a binding domain of characterized affinity and specificity for chicken egg lysozyme as distinct from human milk lysozyme, wherein the binding domain is fused to a biologically or chemically active polypeptide or protein, i.e. β-galactosidase in this embodiment.

13. DEPOSIT OF MICROORGANISMS

The following plasmid was deposited with the American Type Culture Collection (ATCC), Rockville, Md. on Nov. 29, 1988, and has been assigned the indicated accession number:

| Plasmid | Accession Number |
| --- | --- |
| p340 | ATCC 40516 |

The following plasmids were deposited in strain JM-101 with the Agricultural Research Culture Collection and have been assigned the indicated accession numbers:

| Plasmid | Accession Number |
| --- | --- |
| p325-13 | B - 18587 |
| p395-4 | B - 18588 |

The present invention is not to be limited in scope by the plasmids deposited since the deposited embodiments are intended as illustrations of one aspect of the invention, any of which are functionally equivalent within the scope of this invention. Indeed, various modifications of the invention in addition to those shown and described herein will become apparent to those skilled in the art from the foregoing description and accompanying drawings. Such modifications are intended to fall within the scope of the appended claims.

It is also to be understood that all base pair and amino acid residue numbers and sizes given for nucleotides and peptides are approximate and are used for purposes of description.

What is claimed is:

1. A method for identifying a heterofunctional fusion protein having specificity for a ligand of choice, comprising:

(a) inserting into a plurality of vectors (i) one or more of a plurality of different first nucleotide sequences, each first nucleotide sequence comprising a sequence encoding a putative binding domain, said sequence encoding the putative binding domain having been generated totally de novo by random chemical synthesis, and (ii) a second nucleotide sequence encoding a biologically or chemically active effector domain, in which each first nucleotide sequence/second nucleotide sequence combination is located downstream from a 5' ATG start codon to produce a library of vectors coding for in-frame fusion proteins;

(b) transforming compatible host cells with the vectors formed in step (a) to express the fusion proteins; and (c) screening the expressed fusion proteins to identify a fusion protein having binding specificity for the ligand of choice and the desired biological or chemical activity of said effector domain, in which the ligand is selected from the group consisting of a chemical group, an ion, a metal, a peptide or any portion thereof, a nucleic acid or any portion thereof, a carbohydrate, carbohydrate polymer or portion thereof, a lipid, a fatty acid, a viral particle or portion thereof, a membrane vesicle or portion thereof, a cell wall component, a synthetic organic compound, and an inorganic compound.

2. The method according to claim 1, in which the the fusion protein having specificity for a ligand choice is detected by means of the biological or chemical activity of the effector domain encoded by the second nucleotide sequence.

3. The method according to claim 1, in which step (a) further comprises inserting a third nucleotide sequence encoding a linker domain between the first and second nucleotide sequences.

4. The method according to claim 3, in which the linker domain is stable.

5. The method according to claim 3, in which the linker domain moiety is susceptible to cleavage by enzymatic or chemical means.

6. The method according to claim 1, in which the biologically or chemically active effector domain is selected from the group consisting of detectable, enzymatic and therapeutically active polypeptide or protein moieties.

7. The method according to claim 6, in which the biologically or chemically active effector domain is β-galactosidase or a portion thereof.

8. The method according to claim 5, in which the linker domain is susceptible to cleavage by enzymatic means.

9. The method according to claim 8, in which the enzymatic means is selected from the group consisting of collagenase, enterokinase, Factor Xa and thrombin.

10. The method according to claim 5, in which the linker peptide moiety is susceptible to cleavage by chemical means.

11. The method according to claim 10, in which the chemical means is cyanogen bromide.

12. The method according to claim 1, in which the vector is selected from the group consisting of bacterial plasmid, bacterial phage, eukaryotic plasmid and eukaryotic viral vectors.

13. The method according to claim 12, in which the vector is selected from the group consisting of p340, pBR322, pAC1005, pSC101, pBR325, lambda, M13, T7, T4, SV40, EBV, adenovirus, vaccinia, yeast vectors, insect vectors, and derivatives thereof.

14. The method according to claim 13, in which the vector is p340.

15. A method for producing a unifunctional polypeptide or protein having specificity for a ligand of choice, comprising: chemically synthesizing the polypeptide or protein having an amino acid sequence of the binding domain of a fusion protein identified according to the method of claim 1.

16. A method for producing a unifunctional polypeptide or protein having specificity for a ligand of choice, comprising recovering the heterofunctional fusion protein identified according to claim 5, and cleaving said unifunctional polypeptide or protein by enzymatic or chemical means.

17. A method for identifying a heterofunctional fusion protein having specificity for a ligand of choice, comprising:

screening fusion proteins expressed by host cells transformed with a library of vectors coding for in-frame fusion proteins to express the fusion proteins, said library being formed by inserting into a plurality of vectors (i) one or more of a plurality of different first nucleotide sequences, each first nucleotide sequence comprising a sequence encoding a putative binding domain, said sequence encoding the putative binding domain having been generated totally de novo by random chemical synthesis, and (ii) a second nucleotide sequence encoding a biologically or chemically active effector domain, in which each first nucleotide sequence/second nucleotide sequence combination is located downstream from a 5' ATG start codon to produce said library of vectors coding for in-frame fusion proteins to identify a fusion protein having binding specificity for the ligand of choice and the desired biological or chemical activity, in which the ligand is selected from the group consisting of a chemical group, an ion, a metal, a peptide or any portion thereof, a nucleic acid or any portion thereof, a carbohydrate, carbohydrate polymer or portion thereof, a lipid, a fatty acid, a viral particle or portion thereof, a membrane vesicle or portion thereof, a cell wall component, a synthetic organic compound, and an inorganic compound.

* * * * *